US012599428B2

(12) United States Patent
Hase

(10) Patent No.: US 12,599,428 B2
(45) Date of Patent: Apr. 14, 2026

(54) ENERGY TREATMENT TOOL AND TREATMENT SYSTEM

(71) Applicant: OLYMPUS CORPORATION, Hachioji (JP)

(72) Inventor: Hidenosuke Hase, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 935 days.

(21) Appl. No.: 17/380,868

(22) Filed: Jul. 20, 2021

(65) Prior Publication Data

US 2021/0346086 A1 Nov. 11, 2021

Related U.S. Application Data

(63) Continuation of application No. PCT/JP2020/001564, filed on Jan. 17, 2020.

(30) Foreign Application Priority Data

Jan. 23, 2019 (WO) ................. PCT/JP2019/002149

(51) Int. Cl.
*A61B 18/14* (2006.01)
*A61B 17/29* (2006.01)
*A61B 18/00* (2006.01)

(52) U.S. Cl.
CPC .. *A61B 18/1447* (2013.01); *A61B 2017/2925* (2013.01); *A61B 2018/00702* (2013.01); *A61B 2018/00952* (2013.01)

(58) Field of Classification Search
CPC ........ A61B 18/1447; A61B 2017/2925; A61B 2018/00702; A61B 2018/00952
See application file for complete search history.

(56) References Cited

U.S. PATENT DOCUMENTS 10,758,233 B2 * 9/2020 Scheib ................ A61B 17/068
2007/0239029 A1 10/2007 Okabe et al.
(Continued)

FOREIGN PATENT DOCUMENTS

CN 203468669 U 3/2014
EP 3 065 653 A1 9/2016
(Continued)

OTHER PUBLICATIONS

Sep. 22, 2022 Extended European Search Report issued in European Patent Application No. 20745804.3.
(Continued)

*Primary Examiner* — Joseph A Stoklosa
*Assistant Examiner* — Annie L Shoulder
(74) *Attorney, Agent, or Firm* — Oliff PLC

(57) ABSTRACT

An energy treatment tool includes: a grip to be held by an operator; a lever that is provided in a state of being exposed to an outside of the grip, the lever being configured to move in response to a changing operation by an operator, the changing operation being for changing an output state of energy; an electric switch that is arranged inside the grip the electric switch being configured to generate a signal for changing an output state of the energy; and a driver that is installed inside the grip such that the driver is rotatable about an axis intersecting an axis along a longitudinal axis correspondingly to movement of the lever, the driver being configured to switch the electric switch between a contacting state and a noncontacting state.

19 Claims, 27 Drawing Sheets

(56)                References Cited

U.S. PATENT DOCUMENTS

| | | | | |
|---|---|---|---|---|
| 2008/0177134 A1* | 7/2008 | Miyamoto | ........... | A61B 17/062 |
| | | | | 600/104 |
| 2010/0274160 A1* | 10/2010 | Yachi | .................... | H01H 13/08 |
| | | | | 606/1 |
| 2012/0010539 A1 | 1/2012 | Yachi et al. | | |
| 2015/0032150 A1* | 1/2015 | Ishida | ................ | A61B 18/1482 |
| | | | | 606/205 |
| 2015/0335347 A1* | 11/2015 | Hirai | .............. | A61B 17/320092 |
| | | | | 606/169 |
| 2016/0074105 A1* | 3/2016 | Garrison | ............ | A61B 18/1482 |
| | | | | 606/41 |
| 2017/0014129 A1* | 1/2017 | Shelton, IV | ......... | A61B 17/068 |
| 2017/0095249 A1* | 4/2017 | Ichikawa | ........... | A61B 17/0625 |
| 2017/0172606 A1* | 6/2017 | Riestenberg | ... | A61B 17/320092 |
| 2020/0078040 A1 | 3/2020 | Riestenberg et al. | | |

FOREIGN PATENT DOCUMENTS

| | | | |
|---|---|---|---|
| EP | 3 162 309 A1 | 5/2017 | |
| JP | 2000-271142 A | 10/2000 | |
| JP | 2006-218280 A | 8/2006 | |
| JP | 2007-275291 A | 10/2007 | |
| JP | 2011-189185 A | 9/2011 | |
| WO | 2010/122901 A1 | 10/2010 | |
| WO | 2014/196419 A1 | 12/2014 | |
| WO | 2015069719 A1 | 5/2015 | |
| WO | 2017/090191 A1 | 6/2017 | |
| WO | 2017/106235 A1 | 6/2017 | |

OTHER PUBLICATIONS

Mar. 24, 2020 International Search Report issued in International Patent Application No. PCT/JP2020/001564.
Sep. 13, 2022 Office Action issued in Japanese Patent Application No. 2020-568128.

* cited by examiner 63         8C

8C

81

+Z

+Y

+X

Ar2     Ar1

ENERGY TREATMENT TOOL AND TREATMENT SYSTEM

CROSS-REFERENCE TO RELATED APPLICATION

This application is a continuation of International Application No. PCT/JP2020/001564 filed on Jan. 17, 2020, which designates the United States, incorporated herein by reference, and which claims the benefit of priority from International Application No. PCT/JP2019/002149, filed on Jan. 23, 2019, incorporated herein by reference.

BACKGROUND

1. Technical Field

The disclosure relates to energy treatment tools and treatment systems.

2. Related Art

In the related art. an energy treatment tool for applying energy to a site to be treated in a living tissue (hereinafter, referred to as a target site) to treat the target site has been known (see, for example, Japanese Patent Application Laid-open No. 2011-189185).

The energy treatment tool described in Japanese Patent Application Laid-open No. 2011-189185 includes: an end effector for treating the target site by application of energy; and a grip that supports the end effector and is held by an operator. Furthermore, a pair of push buttons are provided respectively on both side surfaces of the grip, the pair of push buttons being for receiving a changing operation by the operator, such as a surgeon. This changing operation is an operation for changing output state of the energy to be applied to the target site. That is, when one of the pair of push buttons is pressed, the output state of the energy applied to the target site is changed.

SUMMARY

In some embodiments, an energy treatment tool includes: a grip to be held by an operator; a lever that is provided in a state of being exposed to an outside of the grip, the lever being configured to move in response to a changing operation by an operator, the changing operation being for changing an output state of energy; an electric switch that is arranged inside the grip the electric switch being configured to generate a signal for changing an output state of the energy; and a driver that is installed inside the grip such that the driver is rotatable about an axis intersecting an axis along a longitudinal axis correspondingly to movement of the lever, the driver being configured to switch the electric switch between a contacting state and a noncontacting state.

In some embodiments, a treatment system includes: the energy treatment tool; and a controller configured to control operation of the energy treatment tool.

The above and other features, advantages and technical and industrial significance of this disclosure will be better understood by reading the following detailed description of presently preferred embodiments of the disclosure, when considered in connection with the accompanying drawings.

DETAILED DESCRIPTION

Modes for implementing the disclosure (hereinafter, embodiments) will be described below while reference is made to the drawings. The disclosure is not limited by the embodiments described below. Furthermore, any portions that are the same will be assigned with the same reference sign, throughout the drawings.

First Embodiment

Schematic Configuration of Treatment System

Figure 1:
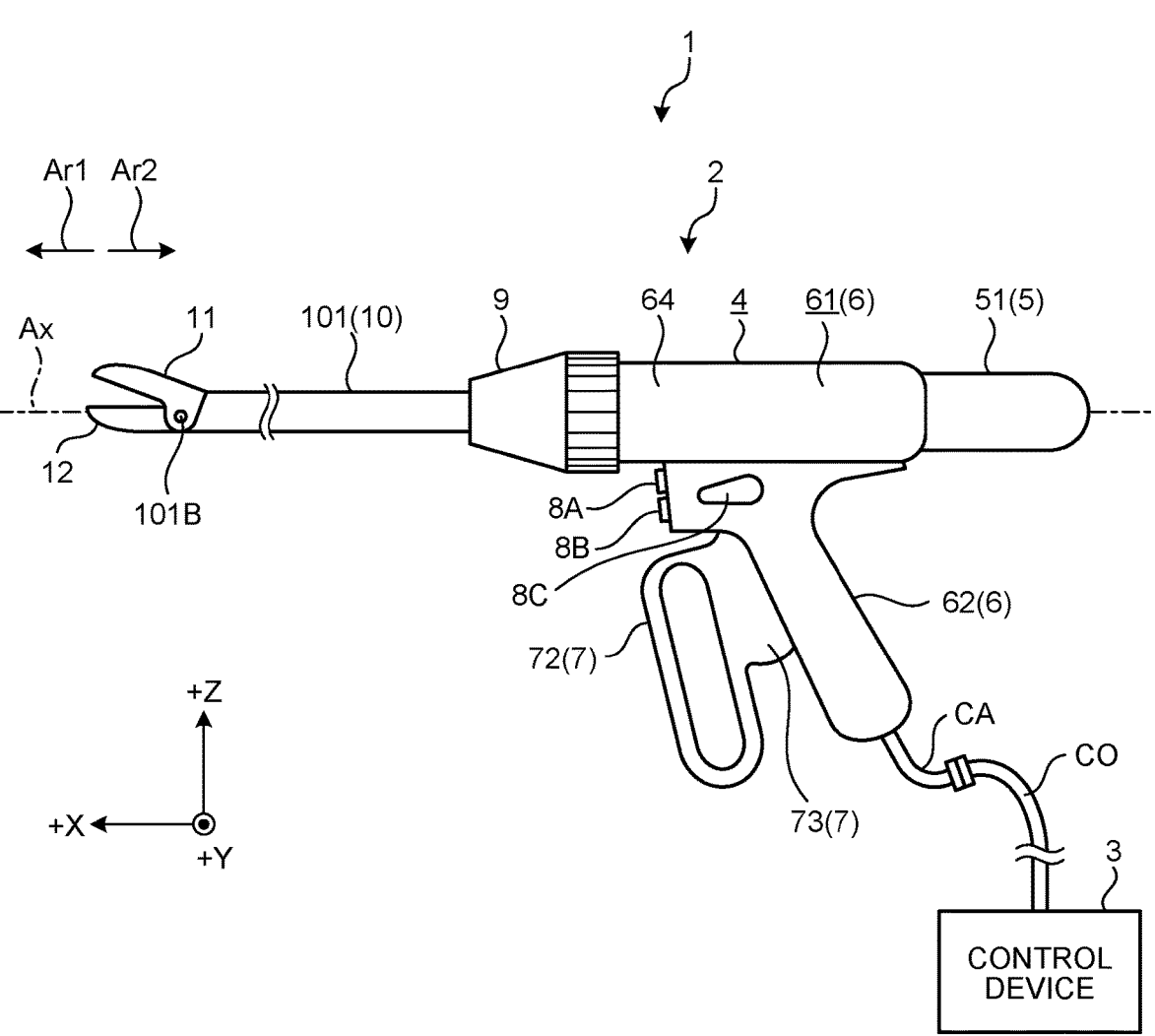
FIG. 1 is a diagram illustrating a treatment system according to a first embodiment.

FIG. 1 is a diagram illustrating a schematic configuration of a treatment system 1 according to a first embodiment.

The treatment system 1 is for applying ultrasound energy and high frequency energy to a site to be treated in a living tissue (hereinafter, referred to as a target site) to treat the target site. Treatment that is able to be executed by the treatment system 1 according to the first embodiment is treatment, such as coagulation (sealing) of the target site, or incision of the target site. Furthermore, the treatment may also be treatment in which the coagulation and the incision are performed at the same time. The treatment system 1 includes, as illustrated in FIG. 1, an energy treatment tool 2 and a control device 3.

Configuration of Energy Treatment Tool

In explanation of a configuration of the energy treatment tool 2, X, Y, and Z coordinate axes that are an X-axis, a-Y-axis, and a Z-axis, which are orthogonal to one another, will hereinafter be used. The X-axis is an axis parallel to a central axis Ax (FIG. 1) of a sheath 10. The central axis Ax corresponds to a longitudinal axis. The Y-axis is an axis orthogonal to the plane of paper of FIG. 1. The Z-axis is an axis along an up-down direction of FIG. 1. Furthermore, one direction along the central axis Ax (a positive direction along the X-axis) will hereinafter be referred to as a distal direction Ar1 and the other direction along the central axis Ax (a negative direction along the X-axis) will hereinafter be referred to as a proximal direction Ar2.

Figure 2:
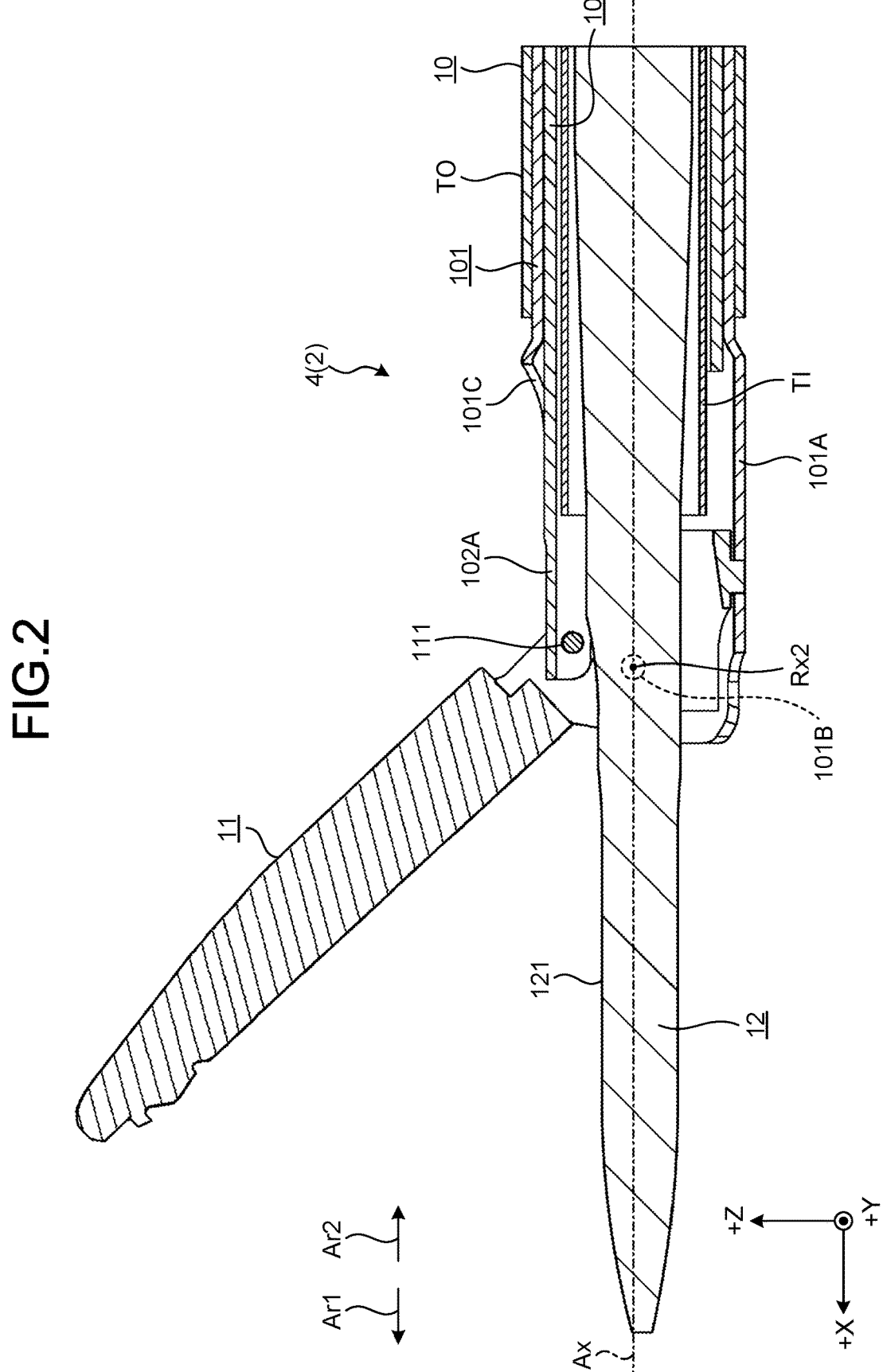
FIG. 2 is a diagram illustrating a configuration of an energy treatment tool.
Figure 3:
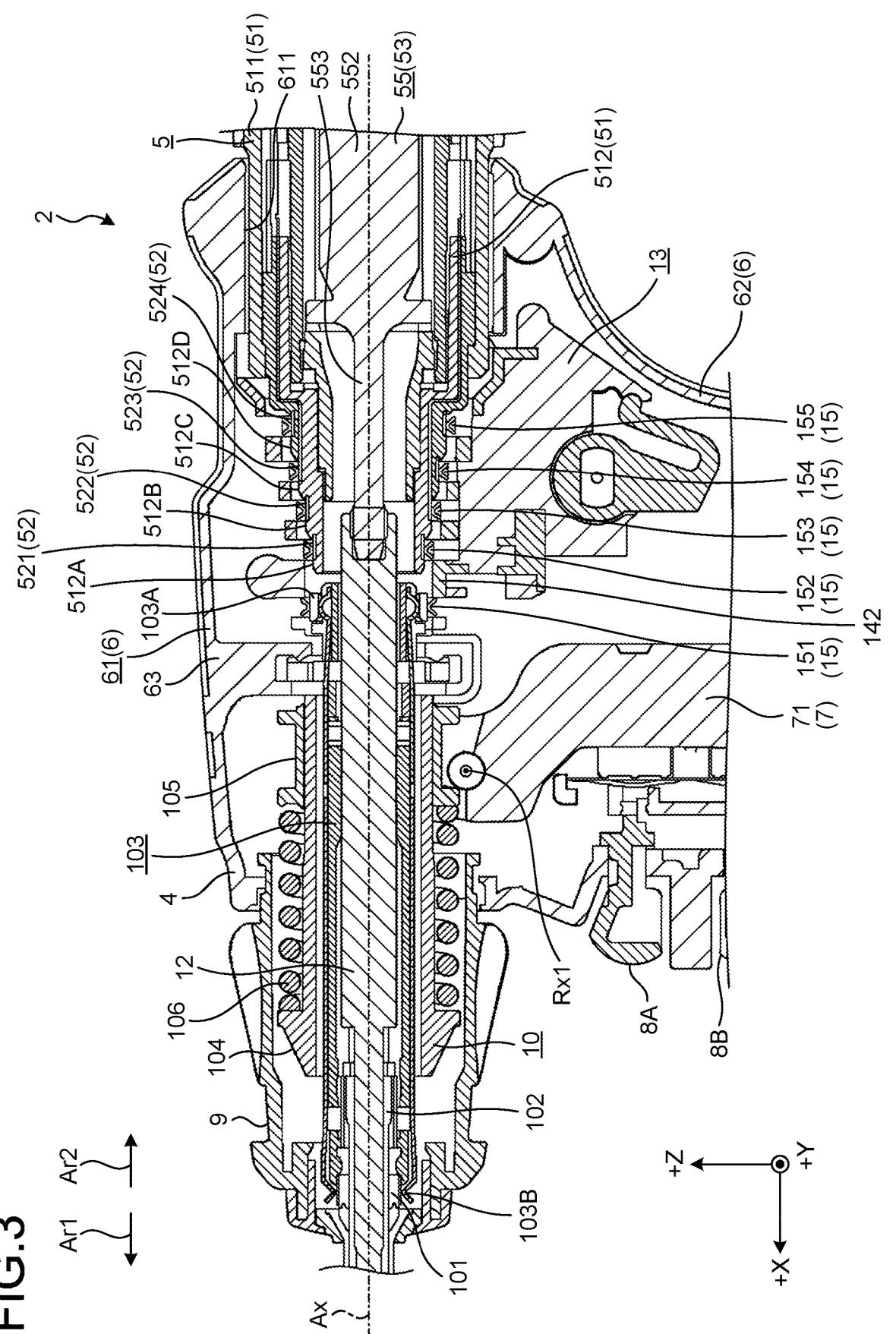
FIG. 3 is a diagram illustrating the configuration of the energy treatment tool.
Figure 4:
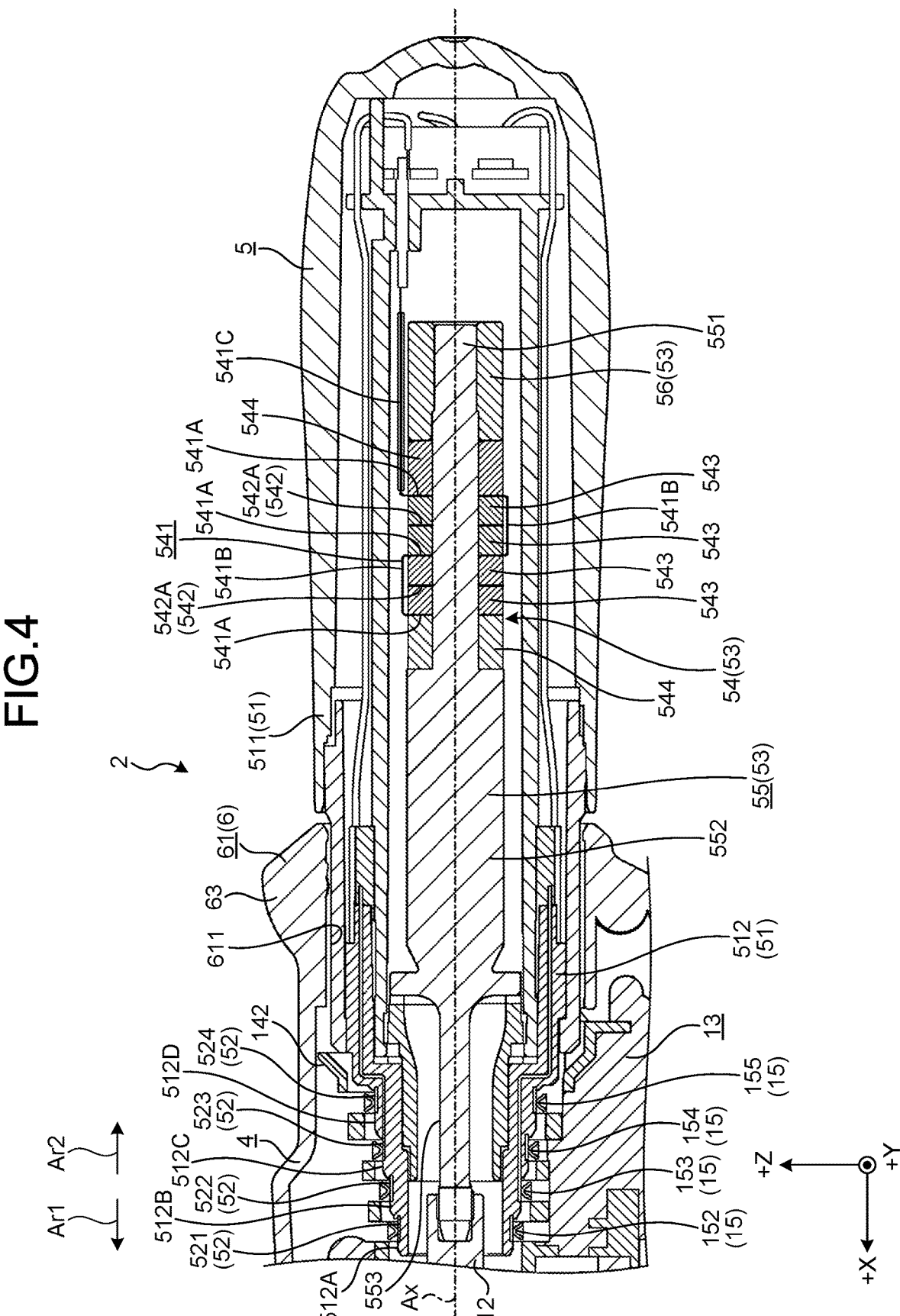
FIG. 4 is a diagram illustrating the configuration of the energy treatment tool.
Figure 5:
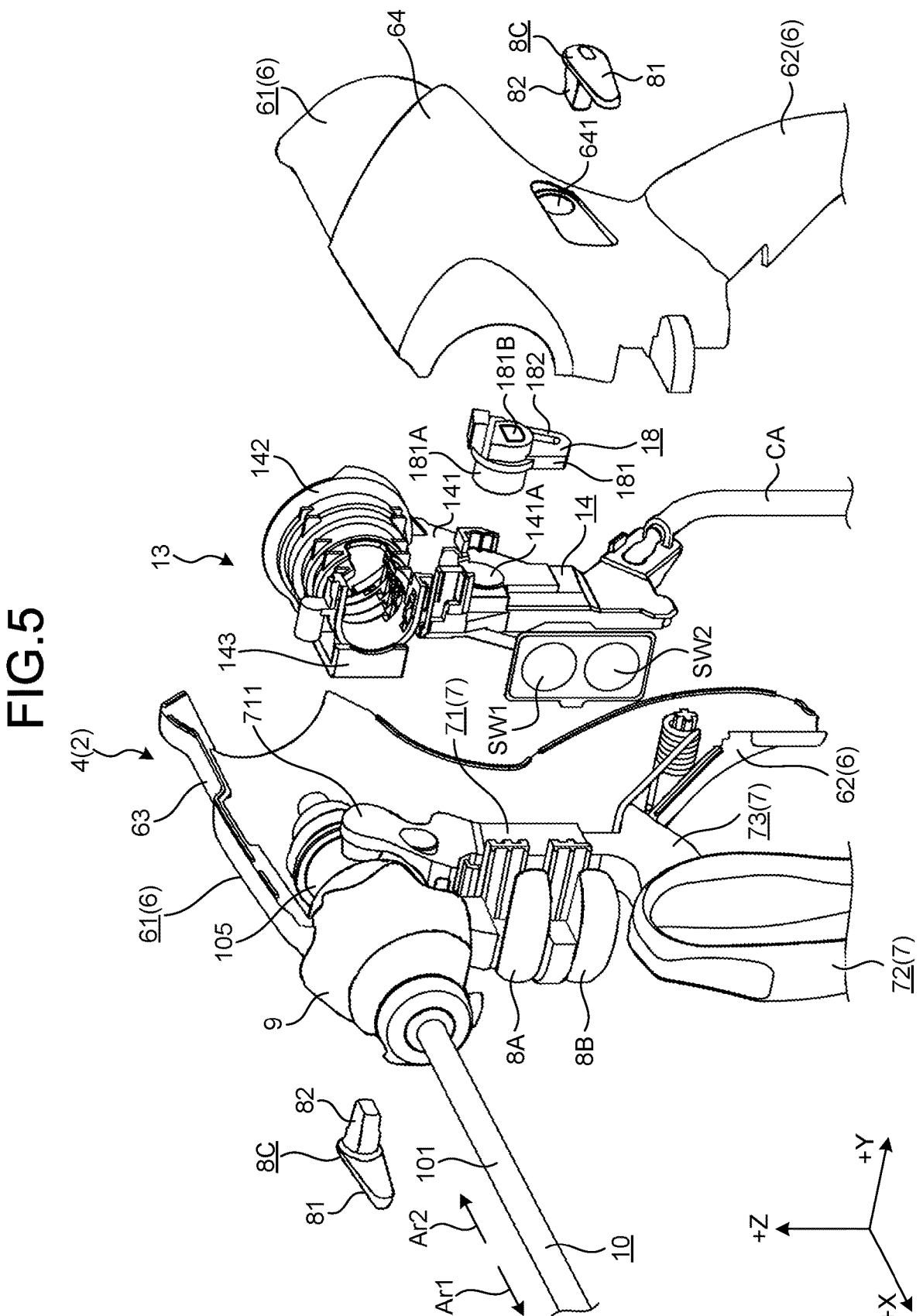
FIG. 5 is a diagram illustrating the configuration of the energy treatment tool.
Figure 6:
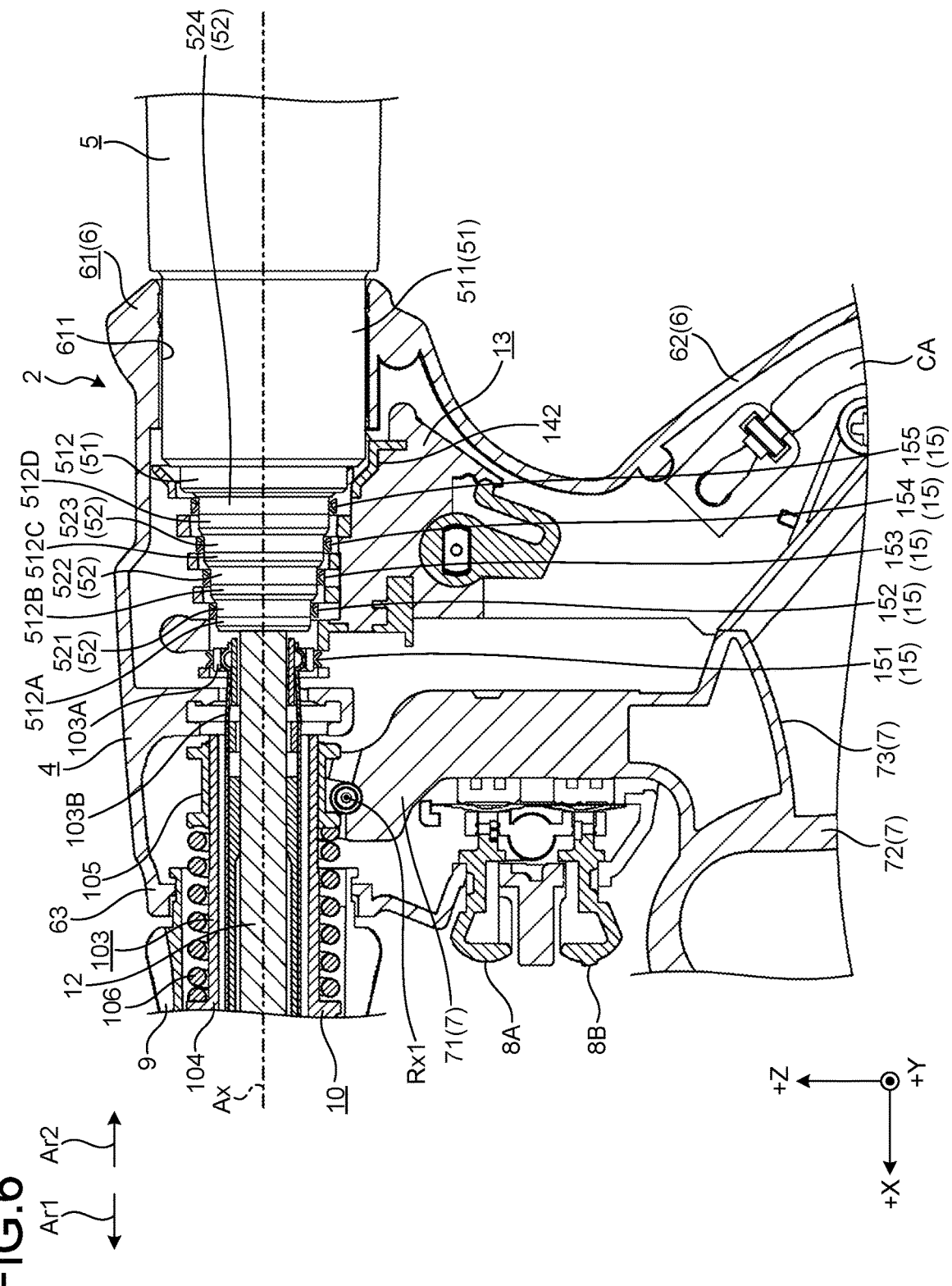
FIG. 6 is a diagram illustrating the configuration of the energy treatment tool.

FIG. 2 to FIG. 6 are diagrams illustrating the configuration of the energy treatment tool 2. Specifically, FIG. 2 to FIG. 4 illustrate, in order from the distal direction Ar1 to the proximal direction Ar2, parts of a sectional view of the energy treatment tool 2, the sectional view having been cut along an X-Z plane including the central axis Ax and viewed from a positive direction along the Y-axis. FIG. 5 and FIG. 6 are diagrams illustrating the interior of a holding case 6. In FIG. 5, for convenience of explanation, illustration of an ultrasound transducer unit 5 has been omitted.

The energy treatment tool 2 is, for example, a medical treatment tool for treating a target site in a state where the medical treatment tool has penetrated an abdominal wall. This energy treatment tool 2 includes, as illustrated in FIG. 1 to FIG. 6, a handpiece 4 and the ultrasound transducer unit 5 (FIG. 1, FIG. 3, FIG. 4, and FIG. 6).

The handpiece 4 includes, as illustrated in FIG. 1 to FIG. 6, the holding case 6 (FIG. 1 and FIG. 3 to FIG. 6), a movable handle 7 (FIG. 1, FIG. 3, FIG. 5, and FIG. 6), a first switch 8A (FIG. 1, FIG. 3, FIG. 5, and FIG. 6), a second switch 8B (FIG. 1, FIG. 3, FIG. 5, and FIG. 6), a pair of third switches 8C (FIG. 1 and FIG. 5), a rotating knob 9 (FIG. 1, FIG. 3, FIG. 5, and FIG. 6), the sheath 10 (FIG. 1 to FIG. 3, FIG. 5, and FIG. 6), a jaw 11 (FIG. 1 and FIG. 2), an ultrasound probe 12 (FIG. 1 to FIG. 4, and FIG. 6), a base unit 13 (FIG. 3 to FIG. 6) and a cable CA (FIG. 1, FIG. 5, and FIG. 6).

The holding case 6 corresponds to a grip. This holding case 6 supports the whole energy treatment tool 2. The holding case 6 includes, as illustrated in FIG. 5, a holding case main body 61 having an approximately cylindrical shape coaxial with the central axis Ax, and a fixed handle 62 that extends downward in FIG. 5 from the holding case main body 61 and is held by an operator, such as a surgeon.

In this first embodiment, the holding case 6 has been divided into two bodies along the X-Z plane including the central axis Ax, as illustrated in FIG. 5. This holding case 6 is formed by combination of these two bodies. One of the two bodies will hereinafter be referred to as a first housing 63 (FIG. 3 to FIG. 6), the one being in a negative direction along the Y-axis, and the other one of the two bodies will hereinafter be referred to as a second housing 64 (FIG. 5), the other one being in the positive direction along the Y-axis.

The movable handle 7 receives each of a closing operation and an opening operation by an operator, such as a surgeon. This movable handle 7 includes, as illustrated in FIG. 5, a handle base portion 71, an operating portion 72, and a connecting portion 73.

The handle base portion 71 is positioned inside the holding case 6. A portion of the handle base portion 71, the portion being in a positive direction along the Z-axis, is rotatably supported about a first rotation axis Rx1 (FIG. 3 and FIG. 6) parallel to the Y-axis, relatively to the holding case 6. Furthermore, a pair of engagement portions 711 (FIG. 5) that protrude in the positive direction along the Z-axis in a forked state and engage with a slider 105 forming the sheath 10 are provided at an end portion of the handle base portion 71, the end portion being in the positive direction along the Z-axis.

The operating portion 72 is a portion that receives each of a closing operation and an opening operation by an operator, such as a surgeon, and is positioned outside the holding case 6, as illustrated in FIG. 5.

The connecting portion 73 is, as illustrated in FIG. 5, a portion provided to extend from the inside to the outside of the holding case 6 and connecting the handle base portion 71 and the operating portion 72 to each other.

The movable handle 7 rotates anticlockwise in FIG. 3 about the first rotation axis Rx1 in a case where the movable handle 7 receives a closing operation by an operator, such as a surgeon. That is, the operating portion 72 moves in a direction to approach the fixed handle 62. On the contrary, the movable handle 7 rotates clockwise in FIG. 3 about the first rotation axis Rx1 in a case where an opening operation for the movable handle 7 is received. That is, the operating portion 72 moves in a direction to separate from the fixed handle 62.

A part of the connecting portion 73 is always positioned inside the holding case 6 from a state where the movable handle 7 has been rotated anticlockwise to the utmost limit in FIG. 3 about the first rotation axis Rx1 by a closing operation to a state where the movable handle 7 has been rotated clockwise to the utmost limit in FIG. 3 about the first rotation axis Rx1 by an opening operation. Upon a closing operation, the distance between the fixed handle 62 and the movable handle 7 decreases. The connecting portion 73 has a shape designed such that the connecting portion 73 does not have any portion with a distance shorter than the outer diameter of the cable CA, the distance being between the fixed handle 62 and the movable handle 7 in the closing operation. The cable CA is thereby prevented from being caught between the fixed handle 62 and the movable handle 7.

The first and second switches 8A and 8B are, as illustrated in FIG. 5, respectively positioned at positions where the first and second housings 63 and 64 are divided, and each provided to be exposed outside from a side surface of the fixed handle 62, the side surface being in the distal direction Ar1. These first and second switches 8A and 8B are configured to be movable in a direction along the central axis Ax.

The first switch 8A receives a first energy output mode setting operation by an operator, such as a surgeon.

Furthermore, the second switch 8B receives a second energy output mode setting operation by an operator, such as a surgeon. The second energy output mode is an energy output mode different from the first energy output mode.

Examples of the first energy output mode include an energy output mode where coagulation and incision of a target site are performed by application of ultrasound energy and high-frequency energy. The first switch 8A is a switch for switching to start of output or stop of output of ultrasound energy and high frequency energy, and corresponds to an output switch. Furthermore, examples of the second energy output mode include an energy output mode where coagulation of a target site is performed by application of high frequency energy. The second switch 8B is a switch for switching to start of output or stop of output of high frequency energy, and corresponds to an output switch.

The pair of third switches 8C correspond to a first lever and a second lever. These pair of third switches 8C are, as illustrated in FIG. 5, respectively provided in a state of facing each other along the Y-axis and being exposed outside from the first and second housings 63 and 64.

The pair of third switches 8C receive a changing operation for changing an output state in at least one energy output mode of the first and second energy output modes (an output state of energy to be applied to a target site) by an operator, such as a surgeon. The changing of the output state in the energy output mode is, for example, switching between a high output mode where driving is performed with a comparatively high voltage and a low output mode where driving is performed with a voltage lower than that in the high output mode. Or, what to switch by the third switches 8C may be freely set by use of the control device 3. A configuration for changing the type of energy (ultrasound energy or high frequency energy) to be applied to a target site according to a changing operation (a configuration for switching to an output state where both ultrasound energy and high frequency energy are applied to a target site or to an output state where only high frequency energy is applied to the target site) may be adopted, without being limited to the configuration for increasing (high output mode) or decreasing (low output mode) electric power according to a changing operation.

The pair of third switches 8C are each supported about an axis by the base unit 13 and move in association with each other according to a changing operation by an operator, such as a surgeon. A structure of the third switches 8C and a support structure for the third switches 8C by means of the base unit 13 will be described in a later section, "Configuration of Base Unit".

The rotating knob 9 has an approximately cylindrical shape coaxial with the central axis Ax and is provided, as illustrated in FIG. 5, on one side of the holding case main body 61, the one side being in the distal direction Ar1. The rotating knob 9 receives a rotating operation by an operator, such as a surgeon. By the rotating operation, the rotating knob 9 is rotated about the central axis Ax, relatively to the holding case main body 61. Furthermore, the jaw 11 and the ultrasound probe 12 are rotated about the central axis Ax by the rotation of the rotating knob 9.

The sheath 10 has an approximately cylindrical shape on the whole. This sheath 10 includes, as illustrated in FIG. 1 to FIG. 3, FIG. 5, or FIG. 6, an outer pipe 101 (FIG. 1 to FIG. 3, and FIG. 5), an inner pipe 102 (FIG. 2 and FIG. 3), a probe holder 103 (FIG. 3 and FIG. 6), a slider receiver 104 (FIG. 3 and FIG. 6), and a slider 105 (FIG. 3, FIG. 5, and FIG. 6).

The outer pipe 101 is a cylindrical pipe formed of an electrically conducting material, such as metal.

The ultrasound probe 12 vibrates with large ultrasound energy. Therefore, when the ultrasound probe 12 that is vibrating comes into contact with the outer pipe 101 formed of, for example, metal, the ultrasound probe 12 may be damaged. Furthermore, as described later, the ultrasound probe 12 and the outer pipe 101 serve as an electric path where high frequency energy flows and thus need to be configured to not come into contact with each other. Therefore, a tube expanding portion 101A expanded in diameter than the other part of the outer pipe 101 is provided at an end portion of the outer pipe 101, as illustrated in FIG. 2, the end portion being in the distal direction Ar1, so that the outer pipe 101 is prevented from coming into contact with the ultrasound probe 12.

Furthermore, an outer peripheral surface of the other part of the outer pipe 101, the other part being other than the tube expanding portion 101A, is covered by an outer tube TO (FIG. 2 and FIG. 3) that is electrically insulating.

In this first embodiment, the tube expanding portion 101A has a length (a length along the central axis Ax) set to, for example, about 5 mm to 15 mm. That is, by making the length of the tube expanding portion 101A as short as possible, the exposed portion of the outer pipe 101 is reduced and the outer pipe 101 is prevented from coming into contact with the ultrasound probe 12.

Furthermore, a first pin 101B (FIG. 1 and FIG. 2) that extends in a direction orthogonal to the plane of paper of FIG. 1 and FIG. 2 and that supports the jaw 11 where the jaw 11 rotates about a second rotation axis Rx2 (FIG. 2) is fixed to the tube expanding portion 101A.

In addition, a notched portion 101C that extends in the proximal direction Ar2 from a distal end of the tube expanding portion 101A is formed in the tube expanding portion 101A, the notched portion 101C being in the positive direction along the Z-axis.

The inner pipe 102 is a cylindrical pipe having a diameter with a dimension smaller than that of the outer pipe 101. Furthermore, the inner pipe 102 is inserted through the outer pipe 101 in a state of being coaxial with the outer pipe 101.

An arm portion 102A that protrudes in the distal direction Ar1 is provided, as illustrated in FIG. 2, in the inner pipe 102, the arm portion 102A being in the positive direction along the Z-axis at an end portion of the inner pipe 102, the end portion being in the distal direction Ar1. A second pin 111 provided in the jaw 11 and extending parallel to the second rotation axis Rx2 (a first pin 101B) is inserted through this arm portion 102A.

The probe holder 103 is formed of a material that is electrically insulating, such as resin, and has an approximately cylindrical shape. This probe holder 103 is inserted through the rotating knob 9 and the holding case main body 61, in a state of extending over the rotating knob 9 and the holding case main body 61, as illustrated in FIG. 3. The probe holder 103 holds the ultrasound probe 12 inserted inside the probe holder 103. Furthermore, the probe holder 103 is mechanically connected, at an end portion of the probe holder 103, to the rotating knob 9 and the outer pipe 101, the end portion being in the distal direction Ar1. That is, the probe holder 103, the outer pipe 101, the jaw 11, and the ultrasound probe 12 rotate, together with the rotating knob 9, about the central axis Ax, in response to a rotating operation on the rotating knob 9 by an operator, such as a surgeon.

An HF active electrode terminal 103A and an electric path 103B are provided, as illustrated in FIG. 3 or FIG. 6, in this probe holder 103.

The HF active electrode terminal 103A is formed of an electrically conducting material and has a ring shape extending over the entire circumferential periphery about the central axis Ax. Furthermore, the HF active electrode terminal 103A is attached to an outer peripheral surface of the probe holder 103, the outer peripheral surface being in the proximal direction Ar2. The HF active electrode terminal 103A is electrically connected to an HF active electrode terminal 151 (FIG. 3 and FIG. 6) provided in the base unit 13. Because the HF active electrode terminal 103A has a ring shape as described above, even if the HF active electrode terminal 103A has rotated about the central axis Ax relatively to the HF active electrode terminal 151 in response to a rotating operation performed on the rotating knob 9 by an operator, such as a surgeon, the HF active electrode terminal 103A is connected electrically to the HF active electrode terminal 151 continuously.

The electric path 103B is formed of an electrically conducting material and extends from an end portion of an outer peripheral surface of the probe holder 103 to another end portion of the outer peripheral surface, the end portion being in the proximal direction Ar2, the other end portion being in the distal direction Ar1. The end portion of the electric path 103B, the end portion being in the proximal direction Ar2, is electrically connected to the HF active electrode terminal 103A, and the other end portion of the electric path 103B, the other end portion being in the distal direction Ar1, is electrically connected to the outer pipe 101, as illustrated in FIG. 3.

The slider receiver 104 is formed of a material that is electrically insulating, such as resin, and has an approximately cylindrical shape. The slider receiver 104 is provided movably along the central axis Ax, relatively to the probe holder 103 in a state where the probe holder 103 has been inserted inside the slider receiver 104. An end portion of the slider receiver 104, the end portion being in the distal direction Ar1, is fixed to an end portion of the inner pipe 102, the end portion being in the proximal direction Ar2, in a state of being restrained from rotating about the central axis Ax while being allowed to move along the central axis Ax, relatively to the probe holder 103. That is, the slider receiver 104 and the inner pipe 102 rotate, together with the rotating knob 9, about the central axis Ax, in response to a rotating operation on the rotating knob 9 by an operator, such as a surgeon.

The slider 105 has an approximately cylindrical shape and is provided movably along the central axis Ax, relatively to the slider receiver 104, in a state where the slider receiver 104 has been inserted through the slider 105. The slider 105 is engaged with the movable handle 7 by the pair of engagement portions 711, as described above.

The slider 105, the slider receiver 104, and the inner pipe 102 operate as described below, in response to operations on the movable handle 7 by an operator, such as a surgeon.

In response to a closing operation on the movable handle 7 by an operator, such as a surgeon, the slider 105 is pushed in the distal direction Ar1 along the central axis Ax by the pair of engagement portions 711.

Furthermore, the slider receiver 104 receives a pressing force in the distal direction Ar1 from the slider 105 via a coil spring 106 (FIG. 3 and FIG. 6) provided between the slider receiver 104 and the slider 105. In addition, the inner pipe 102 moves in the distal direction Ar1 along the central axis Ax, in association with the slider receiver 104. What is more, the arm portion 102A pushes the second pin 111 in the distal direction Ar1. The jaw 11 then rotates anticlockwise in FIG. 2 about the second rotation axis Rx2. In this rotation, because the second pin 111 also moves in a state of maintaining a certain distance about the second rotation axis Rx2, the arm portion 102A moves in the distal direction Ar1 while being deformed in the positive direction along the Z-axis where the notched portion 101C has been provided. That is, the jaw 11 moves in a direction (a closing direction) to approach an end portion 121 (FIG. 2) of the ultrasound probe 12, the end portion 121 being in the distal direction Ar1.

Furthermore, in response to an opening operation on the movable handle 7 by an operator, such as a surgeon, the jaw 11 rotates clockwise in FIG. 2 about the second rotation axis Rx2. That is, the jaw 11 moves in a direction (an opening direction) to separate from the end portion 121 of the ultrasound probe 12, the end portion 121 being in the distal direction Ar1.

As described above, in response to an operation on the movable handle 7 by an operator, such as a surgeon, the jaw 11 opens or closes relatively to the end portion 121 of the ultrasound probe 12, the end portion 121 being in the distal direction Ar1.

In this first embodiment, the arm portion 102A has a length (a length along the central axis Ax) set to, for example, about 5 mm to 10 mm. That is, making the length of the arm portion 102A as short as possible, prevents contact between the arm portion 102A and the outer pipe 101 upon deformation of the arm portion 102A in association with opening or closing of the jaw 11. Furthermore, making the cross-sectional shape along the direction orthogonal to the central axis Ax into an approximate U-shape or a broad shape strengthens the arm portion 102A, and contact between the arm portion 102A and the outer pipe 101 upon deformation of the arm portion 102A in association with opening or closing of the jaw 11 is thereby avoided. Decrease in the opening or closing force of the jaw 11 (the force for holding a target site) is thereby able to be prevented.

Furthermore, in this first embodiment, a distance between an outer surface of the arm portion 102A and the central axis Ax is set to be equal to or less than a distance between an outer peripheral surface of a part of the inner pipe 102 and the central axis Ax, the part being a part other than the arm portion 102A. The arm portion 102A is thereby prevented from sliding against an inner surface of the outer pipe 101 when the inner pipe 102 is inserted into the outer pipe 101 from a proximal end of the outer pipe 101. That is, the ease of installation of the inner pipe 102 in the outer pipe 101 is able to be improved.

Figure 7:
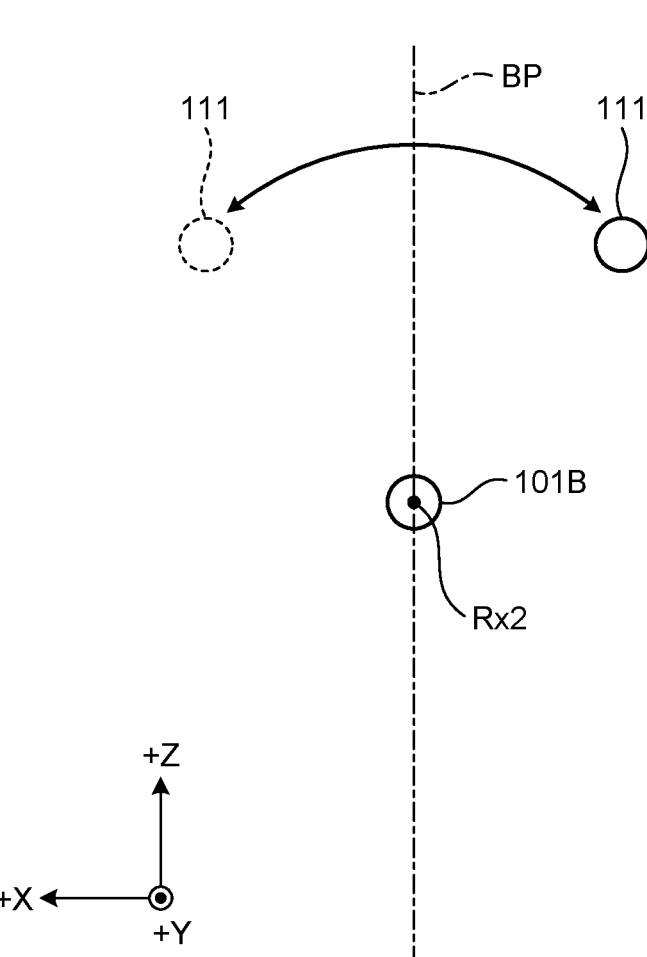
FIG. 7 is a diagram illustrating a positional relation between a first pin and a second pin.

FIG. 7 is a diagram illustrating a positional relation between the first and second pins 101B and 111. Specifically, FIG. 7 is a diagram of the first and second pins 101B and 111 as viewed along the direction orthogonal to the plane of paper of FIG. 2. In FIG. 7, the second pin 111 in a state where the jaw 11 is open is illustrated with a solid line and the second pin 111 in a state where the jaw 11 is closed is illustrated with a broken line.

In this first embodiment, as illustrated in FIG. 7, a Y-Z plane BP (FIG. 7) passing the second rotation axis Rx2 is set to pass between the position of the second pin 111 in the state where the jaw 11 is open and the position of the second pin 111 in the state where the jaw 11 is closed. The second pin 111 in the state where the jaw 11 is open and the second pin 111 in the state where the jaw 11 is closed are preferably set to be at positions symmetrical to each other about the plane BP. The amount of deformation of the arm portion 102A in a Z-axis direction in association with opening or closing of the jaw 11 is thereby able to be minimized and the amount of force associated with movement of the inner pipe 102 along the central axis Ax is able to be converted without loss to the amount of force for opening or closing the jaw 11 (the amount of force for holding a target site).

At least a part of the jaw 11 is formed of an electrically conducting material. The jaw 11 is electrically connected to the HF active electrode terminal 103A via the outer pipe 101 and the electric path 103B.

The ultrasound probe 12 is formed of an electrically conducting material and has an elongated shape linearly extending along the central axis Ax. Furthermore, the ultrasound probe 12 is inserted through the sheath 10 in a state where the end portion 121 in the distal direction Ar1 protrudes outside, as illustrated in FIG. 2. As this is done, an end portion of the ultrasound probe 12, the end portion being in the proximal direction Ar2, is mechanically connected to the ultrasound transducer unit 5, as illustrated in FIG. 3 or FIG. 6. That is, the ultrasound transducer unit 5 rotates, together with the ultrasound probe 12, about the central axis Ax, in response to a rotating operation on the rotating knob 9 by an operator, such as a surgeon. The ultrasound probe 12 transmits ultrasound vibration generated by the ultrasound transducer unit 5, to the end portion 121 in the distal direction Ar1 from the end portion in the proximal direction Ar2. In this first embodiment, the ultrasound vibration is longitudinal vibration that is vibration in a direction along the central axis Ax.

An outer peripheral surface of the ultrasound probe 12 is covered by an inner tube TI (FIG. 2) that is electrically insulating, to provide electric insulation between the outer pipe 101 or the inner pipe 102 and the ultrasound probe 12.

The cable CA is detachably connected to an electric cable C0 (FIG. 1) extending from the control device 3. That is, the cable CA is electrically connected to the control device 3 via the electric cable C0.

The cable CA is attached to the base unit 13, and the base unit 13 is provided inside the holding case 6, as illustrated in FIG. 3 to FIG. 6. This base unit 13 has a function of electrically connecting the cable CA to the HF active electrode terminal 103A provided in the probe holder 103 and a first terminal 52 (FIG. 4 and FIG. 6) provided in the ultrasound transducer unit 5, and a function of supporting the pair of third switches 8C.

A detailed configuration of the cable CA and the base unit 13 will be described in a later section, "Configuration of Base Unit".

The ultrasound transducer unit 5 includes, as illustrated in FIG. 4, a transducer unit (TD) case 51, the first terminal 52, and an ultrasound transducer 53.

The TD case 51 supports the first terminal 52 and the ultrasound transducer 53 and is detachably connected to the holding case main body 61. This TD case 51 includes, as illustrated in FIG. 4, a TD case main body 511 and a first terminal holding portion 512.

The TD case main body 511 has a cylindrical shape with a bottom and is connected to the holding case main body 61 in a posture where an opening of the cylindrical shape is in the distal direction Ar1, as illustrated in FIG. 4.

A guiding surface 611 (FIG. 4 and FIG. 6) is provided on a part of an inner surface of the holding case main body 61, the part being in the proximal direction Ar2, the guiding surface 611 linearly extending along the central axis Ax in the distal direction Ar1 from an end portion of the holding case main body 61, the end portion being in the proximal direction Ar2, the guiding surface 611 having an inner diameter with a dimension slightly larger than the dimension of the outer diameter of the TD case main body 511, the guiding surface 611 being cylindrical. An outer peripheral surface of the TD case main body 511 is thereby guided by the guiding surface 611 when the ultrasound transducer unit 5 is inserted through (connected to) the holding case main body 61. A central axis of the ultrasound transducer unit 5 is then in line with the central axis Ax. Whatever the angle at which the ultrasound transducer unit 5 is inserted into the holding case main body 61 is, the ultrasound transducer unit 5 is able to be prevented from colliding with a second terminal holding portion 142 (FIG. 6) provided in the base unit 13.

The first terminal holding portion 512 is a tubular body extending along the central axis Ax and is fitted in the opening of the TD case main body 511, as illustrated in FIG. 4. An outer surface of a portion of the first terminal holding portion 512 is formed in a stepped shape having four steps 512A to 512D in order from the distal end direction Ar1, the portion protruding in the distal direction Ar1 from the TD case main body 511, as illustrated in FIG. 3, FIG. 4, or FIG. 6. These four steps 512A to 512D each have a cross-sectional shape that is circular about the central axis Ax and increase in dimension of the diameter in the order of the four steps 512A to 512D.

The first terminal 52 includes, as illustrated in FIG. 3, FIG. 4, or FIG. 6, an HF return electrode terminal 521, an IR terminal 522, a US return electrode terminal 523, and a US active electrode terminal 524. Each of these terminals 521 to 524 is formed of an electrically conducting material.

The HF return electrode terminal 521 is provided on the step 512A, over the entire circumferential periphery of the circular cross-sectional shape of the step 512A. The HF return electrode terminal 521 is electrically connected to an HF return electrode terminal 152 (FIG. 3, FIG. 4, or FIG. 6) provided in the base unit 13 by connecting the ultrasound transducer unit 5 to the holding case main body 61. Because the HF return electrode terminal 521 is provided over the entire circumferential periphery of the circular cross-sectional shape of the step 512A as described above, the HF return electrode terminal 521 is electrically connected to the HF return electrode terminal 152 continuously even if the HF return electrode terminal 521 is rotated about the central axis Ax relatively to the HF return electrode terminal 152 in response to a rotating operation performed on the rotating knob 9 by an operator, such as a surgeon.

The IR terminal 522 is provided on the step 512B, over the entire circumferential periphery of the circular cross-sectional shape of the step 512B. The IR terminal 522 is electrically connected to an IR terminal 153 (FIG. 3, FIG. 4, or FIG. 6) provided in the base unit 13 by connecting the ultrasound transducer unit 5 to the holding case main body 61. Because the IR terminal 522 is provided over the entire circumferential periphery of the circular cross-sectional shape of the step 512B as described above, the IR terminal 522 is electrically connected to the IR terminal 153 continuously even if the IR terminal 522 is rotated about the central axis Ax relatively to the IR terminal 153 in response to a rotating operation on the rotating knob 9 by an operator, such as a surgeon. Furthermore, the ultrasound transducer unit 5 has a built-in transducer (TD) memory that stores identification information identifying the ultrasound transducer unit 5, for example, although specific illustration thereof has been omitted. The IR terminal 522 is electrically connected to the TD memory via an electric path (not illustrated in the drawings) provided inside the TD case 51.

The US return electrode terminal 523 is provided on the step 512C, over the entire circumferential periphery of the circular cross-sectional shape of the step 512C. The US return electrode terminal 523 is electrically connected to a US return electrode terminal 154 (FIG. 3, FIG. 4, or FIG. 6) described later by connecting the ultrasound transducer unit 5 to the holding case main body 61. Because the US return electrode terminal 523 is provided over the entire circumferential periphery of the circular cross-sectional shape of the step 512C as described above, the US return electrode terminal 523 is electrically connected to the US return electrode terminal 154 continuously even if the US return electrode terminal 523 is rotated about the central axis Ax relatively to the US return electrode terminal 154 in response to a rotating operation on the rotating knob 9 by an operator, such as a surgeon.

The US active electrode terminal 524 is provided on the step 512D, over the entire circumferential periphery of the circular cross-sectional shape of the step 512D. The US active electrode terminal 524 is electrically connected to a US active electrode terminal 155 (FIG. 3, FIG. 4, or FIG. 6) provided in the base unit 13 by connecting the ultrasound transducer unit 5 to the holding case main body 61. Because the US active electrode terminal 524 is provided over the entire circumferential periphery of the circular cross-sectional shape of the step 512D as described above, the US active electrode terminal 524 is electrically connected to the US active electrode terminal 155 continuously even if the US active electrode terminal 524 is rotated about the central axis Ax relatively to the US active electrode terminal 155 in response to a rotating operation on the rotating knob 9 by an operator, such as a surgeon.

The ultrasound transducer 53 generates ultrasound vibration, under control of the control device 3. In this first embodiment, the ultrasound transducer 53 is formed of a bolt-clamped Langevin transducer (BLT). This ultrasound transducer 53 includes, as illustrated in FIG. 4, a transducer main body 54, a front mass 55, and a back mass 56.

The transducer main body 54 includes, as illustrated in FIG. 4, a first electrode plate 541, a second electrode plate 542, and plural (four in this first embodiment) piezoelectric elements 543.

The first and second electrode plates 541 and 542 are parts to which a drive signal that is alternating-current power for generating ultrasound vibration is supplied from the control device 3.

The first electrode plate 541 includes, as illustrated in FIG. 4, plural (three in this first embodiment) negative electrode plates 541A, plural (two in this first embodiment) negative electrode wiring portions 541B, and a negative electrode terminal 541C.

The plural negative electrode plates 541A each have a disk shape with an opening (not illustrated in the drawings) in the center, and are provided on one another along the central axis Ax.

The plural negative electrode wiring portions 541B are portions that electrically connect outer rim portions of the negative electrode plates 541A adjacent to each other together.

The negative electrode terminal 541C extends in the proximal direction Ar2 from an outer rim of one of the plural negative electrode plates 541A, the one being positioned furthest in the proximal direction Ar2. The negative electrode terminal 541C is electrically connected to the US return electrode terminal 523 via an electric path (not illustrated in the drawings) provided inside the TD case 51. That is, the first electrode plate 541 is electrically connected to the US return electrode terminal 523.

The second electrode plate 542 includes, as illustrated in FIG. 4, plural (two in the first embodiment) positive electrode plates 542A, a positive electrode wiring portion (not illustrated in the drawings), and a positive electrode terminal (not illustrated in the drawings).

The plural positive electrode plates 542A each have a disk shape with an opening (not illustrated in the drawings) in the center, and are provided on one another along the central axis Ax. The positive electrode plates 542A have approximately the same shape as the negative electrode plates 541A.

The negative electrode plates 541A and the positive electrode plates 542A are arranged alternately along the central axis Ax, as illustrated in FIG. 4. One of the plural negative electrode plates 541A, the one being positioned furthest in the proximal direction Ar2, is arranged at a position closer to the back mass 56 than one of the plural positive electrode plates 542A is, the one being positioned furthest in the proximal direction Ar2.

The positive electrode wiring portion (not illustrated in the drawings) is a portion that electrically connects outer rim portions of the positive electrode plates 542A adjacent to each other together.

The positive electrode terminal (not illustrated in the drawings) extends in the proximal direction Ar2 from an outer rim of one of the plural positive electrode plates 542A, the one being positioned furthest in the proximal direction Ar2. The positive electrode terminal (not illustrated in the drawings) is electrically connected to the US active electrode terminal 524 via an electric path (not illustrated in the drawings) provided inside the TD case 51. That is, the second electrode plate 542 is electrically connected to the US active electrode terminal 524.

The plural piezoelectric elements 543 each have a disk shape with an opening (not illustrated in the drawings) in the center and are each provided between the negative electrode plate 541A and the positive electrode plate 542A. That is, the plural piezoelectric elements 543 are layered over one another along the central axis Ax. Generation of potential differences in a layering direction along the central axis Ax in response to drive signals supplied to the first and second electrode plates 541 and 542 causes the plural piezoelectric elements 543 to alternately repeat expansion and contraction along the layering direction. The ultrasound transducer 53 thereby generates ultrasound vibration that is longitudinal vibration with a vibrating direction in the layering direction.

The front mass 55 is formed of an electrically conducting material and has an elongated shape linearly extending along the central axis Ax. This front mass 55 includes, as illustrated in FIG. 4, an element attachment portion 551, a sectional area changing portion 552, and a probe attachment portion 553.

The element attachment portion 551 is a bolt linearly extending along the central axis Ax and is inserted through each of: the openings (not illustrated in the drawings) of the plural negative electrode plates 541A, the openings (not illustrated in the drawings) of the plural positive electrode plates 542A, and the openings (not illustrated in the drawings) of the plural piezoelectric elements 543. The back mass 56 that is a nut formed of an electrically conducting material is attached to an end portion of the element attachment portion 551, the end portion being in the proximal direction Ar2, as illustrated in FIG. 4.

The sectional area changing portion 552 is a portion that is provided at an end portion of the element attachment portion 551, the end portion being in the distal direction Ar1, and that amplifies amplitude of ultrasound vibration. Furthermore, an end portion of the sectional area changing portion 552 has a diameter with a dimension set larger than that of the element attachment portion 551, the end portion being in the proximal direction Ar2, and an end portion of the sectional area changing portion 552, the end portion being in the distal direction Ar1, has a conical shape such that the end portion decreases in its cross-sectional area in the distal direction Ar1, as illustrated in FIG. 4. That is, the plural negative electrode plates 541A, the plural positive electrode plates 542A, and the plural piezoelectric elements 543 are integrally fastened together in a state of having an approximately cylindrical shape by being held between the sectional area changing portion 552 and the back mass 56 with the element attachment portion 551 penetrating, along the central axis Ax, through the plural negative electrode plates 541A, the plural positive electrode plates 542A, and the plural piezoelectric elements 543. In this first embodiment, an insulating plate 544 (FIG. 4) that is electrically insulating is interposed each: between the sectional area changing portion 552 and one of the plural negative electrode plates 541A, the one being furthest in the distal direction Ar1; and between the back mass 56 and one of the plural negative electrode plates 541A, the one being furthest in the proximal direction Ar2.

The probe attachment portion 553 is provided at an end portion of the sectional area changing portion 552, the end portion being in the distal direction Ar1, and linearly extends along the central axis Ax, as illustrated in FIG. 4. An end portion of the probe attachment portion 553, the end portion being in the distal direction Ar1, is mechanically and electrically connected to an end portion of the ultrasound probe 12, the end portion being in the proximal direction Ar2, by connecting the ultrasound transducer unit 5 to the holding case main body 61.

The back mass 56 is electrically connected to the HF return electrode terminal 521 via an electric path (not illustrated in the drawings) provided inside the TD case 51. That is, the ultrasound probe 12 is electrically connected to the HF return electrode terminal 521 via the back mass 56 and front mass 55. The HF return electrode terminal 521 is also electrically connected to the built-in TD memory (not illustrated in the drawings) in the ultrasound transducer unit 5 via an electric path (not illustrated in the drawings) provided inside the TD case 51.

Configuration of Control Device

The energy treatment tool 2 is detachably connected to the control device 3 via the electric cable C0. The control device 3 integrally controls operation of the energy treatment tool 2 via the electric cable C0.

Specifically, the control device 3 is electrically connected to the built-in TD memory in the ultrasound transducer unit 5 via the HF return electrode terminal 521, the IR terminal 522, the base unit 13, the cable CA, and the electric cable C0. The control device 3 acquires the identification information identifying the ultrasound transducer unit 5, for example, stored in the TD memory.

Furthermore, the control device 3 is electrically connected to a handpiece memory 161 (see FIG. 12) provided in the base unit 13, via the base unit 13, the cable CA, and the electric cable C0. The control device 3 acquires, for example, identification information identifying the handpiece 4 stored in the handpiece memory 161.

Furthermore, the control device 3 is electrically connected, via the base unit 13, the cable CA, and the electric cable C0, to a first switch element SW1 (FIG. 5) that is provided in the base unit 13 and that detects first energy output mode setting operation on the first switch 8A. That is, the control device 3 enables recognition of whether or not a first energy output mode setting operation has been performed on the first switch 8A. Furthermore, the control device 3 is electrically connected to the first electrode plate

541 via the US return electrode terminal 523, the base unit 13, the cable CA, and the electric cable C0, and is electrically connected to the second electrode plate 542 via the US active electrode terminal 524, the base unit 13, the cable CA, and the electric cable C0. In addition, the control device 3 is electrically connected to the jaw 11 via the outer pipe 101, the electric path 103B, the HF active electrode terminal 103A, the base unit 13, the cable CA, and the electric cable C0, and is electrically connected to the ultrasound probe 12 via the front mass 55, the back mass 56, the HF return electrode terminal 521, the base unit 13, the cable CA, and the electric cable C0.

The control device 3 executes the first energy output mode as described below when a first energy output mode setting operation has been performed on the first switch 8A.

A case where output using ultrasound energy and high frequency energy is performed will be described herein as the first energy output mode. That is, the control device 3 supplies a drive signal to the US return electrode terminal 523 (the first electrode plate 541) and the US active electrode terminal 524 (the second electrode plate 542). The plural piezoelectric elements 543 thereby generate longitudinal vibration (ultrasound vibration) that is vibration along the central axis Ax. Furthermore, the longitudinal vibration causes the end portion 121 of the ultrasound probe 12 to vibrate at desired amplitude, the end portion 121 being in the distal direction Ar1. From the end portion 121, ultrasound vibration is applied to a target site held between the jaw 11 and the end portion 121. In other words, ultrasound energy is applied to the target site from the end portion 121.

Furthermore, the control device 3 supplies a high frequency signal that is high frequency electric power, to the HF active electrode terminal 103A (the jaw 11) and the HF return electrode terminal 521 (the ultrasound probe 12), approximately simultaneously to the application of the ultrasound energy to the target site. High frequency electric current thereby flows in the target site held between the jaw 11 and the end portion 121 of the ultrasound probe 12, the end portion 121 being in the distal direction Ar1. In other words, high frequency energy is applied to the target site.

Frictional heat is then generated between the end portion 121 and the target site by the longitudinal vibration of the end portion 121 of the ultrasound probe 12, the end portion 121 being in the distal direction Ar1. Joule heat is also generated in the target site due to the flow of high frequency electric current. Coagulation (sealing) and incision of the target site are thereby performed. That is, the jaw 11 and the end portion 121 of the ultrasound probe 12, the end portion 121 being in the distal direction Ar1, correspond to an end effector.

Furthermore, the control device 3 is electrically connected, via the base unit 13, the cable CA, and the electric cable C0, to a second switch element SW2 (FIG. 5) that is provided in the base unit 13 and that detects a second energy output mode setting operation on the second switch 8B. That is, the control device 3 enables recognition of whether or not a second energy output mode setting operation has been performed on the second switch 8B.

The control device 3 executes the second energy output mode as described below when a second energy output mode setting operation has been performed on the second switch 8B.

A case where output using high frequency energy is performed will be described herein as the second energy output mode. That is, the control device 3 supplies a high frequency signal that is high frequency electric power, to the HF active electrode terminal 103A (the jaw 11) and the HF return electrode terminal 521 (the ultrasound probe 12). High frequency electric current thereby flows in the target site held between the jaw 11 and the end portion 121 of the ultrasound probe 12, the end portion 121 being in the distal direction Ar1.

Joule heat is then generated in the target site due to the flow of high frequency electric current. Sealing of the target site is thereby performed.

Furthermore, the control device 3 is electrically connected, via the base unit 13, the cable CA, and the electric cable C0, to a third switch element SW3 (see FIG. 13, FIG. 16, or FIG. 17) that is provided in the base unit 13 and that detects a changing operation on the third switch 8C. That is, the control device 3 enables recognition of whether or not a changing operation on the third switch 8C has been performed.

The control device 3 switches the output state in at least one energy output mode of the first and second energy output modes by changing electric power of a drive signal or high frequency signal if a changing operation has been performed on the third switch 8C.

Configuration of Base Unit

Figure 8:
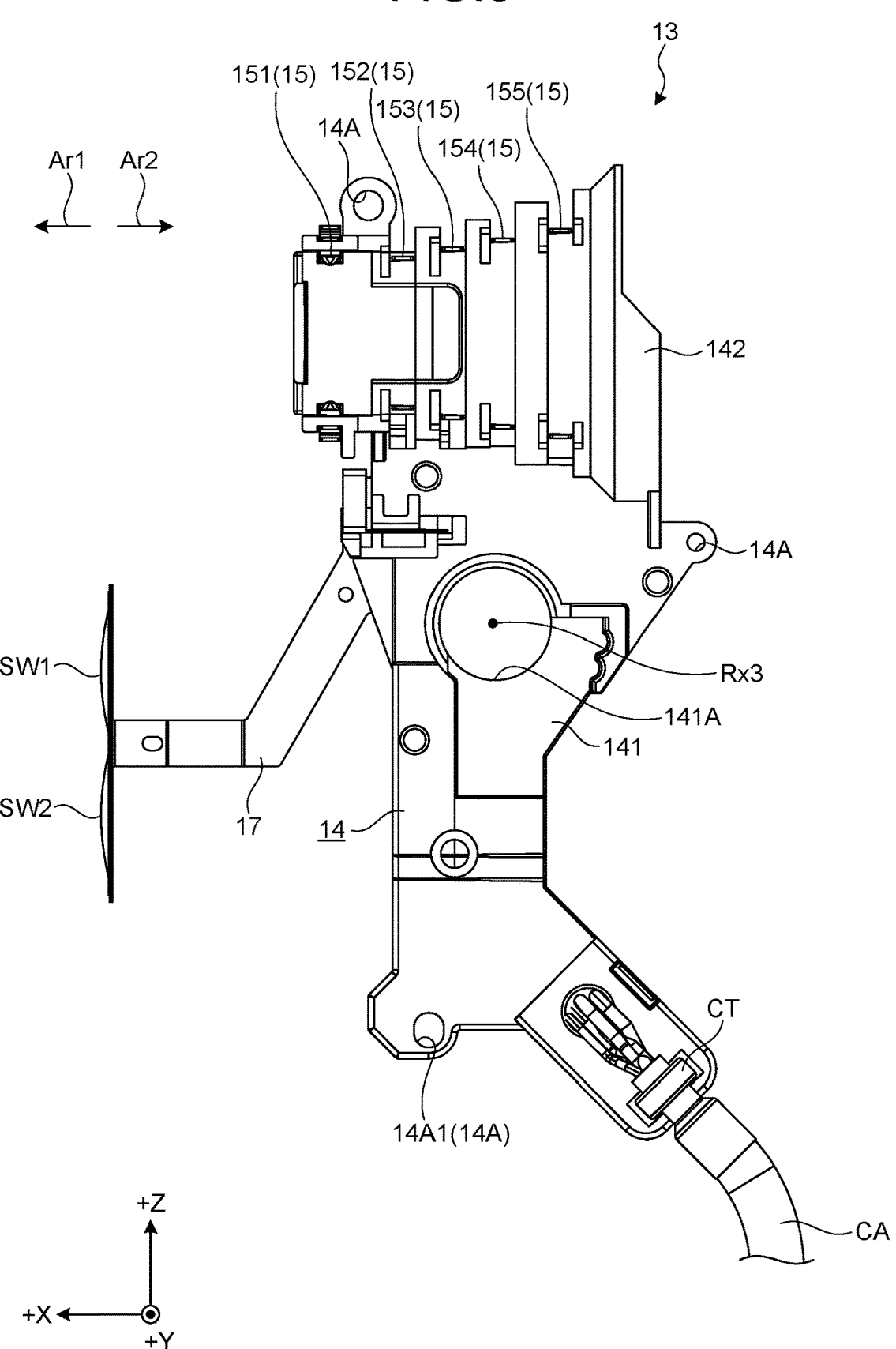
FIG. 8 is a diagram illustrating an overall configuration of a base unit.
Figure 9:
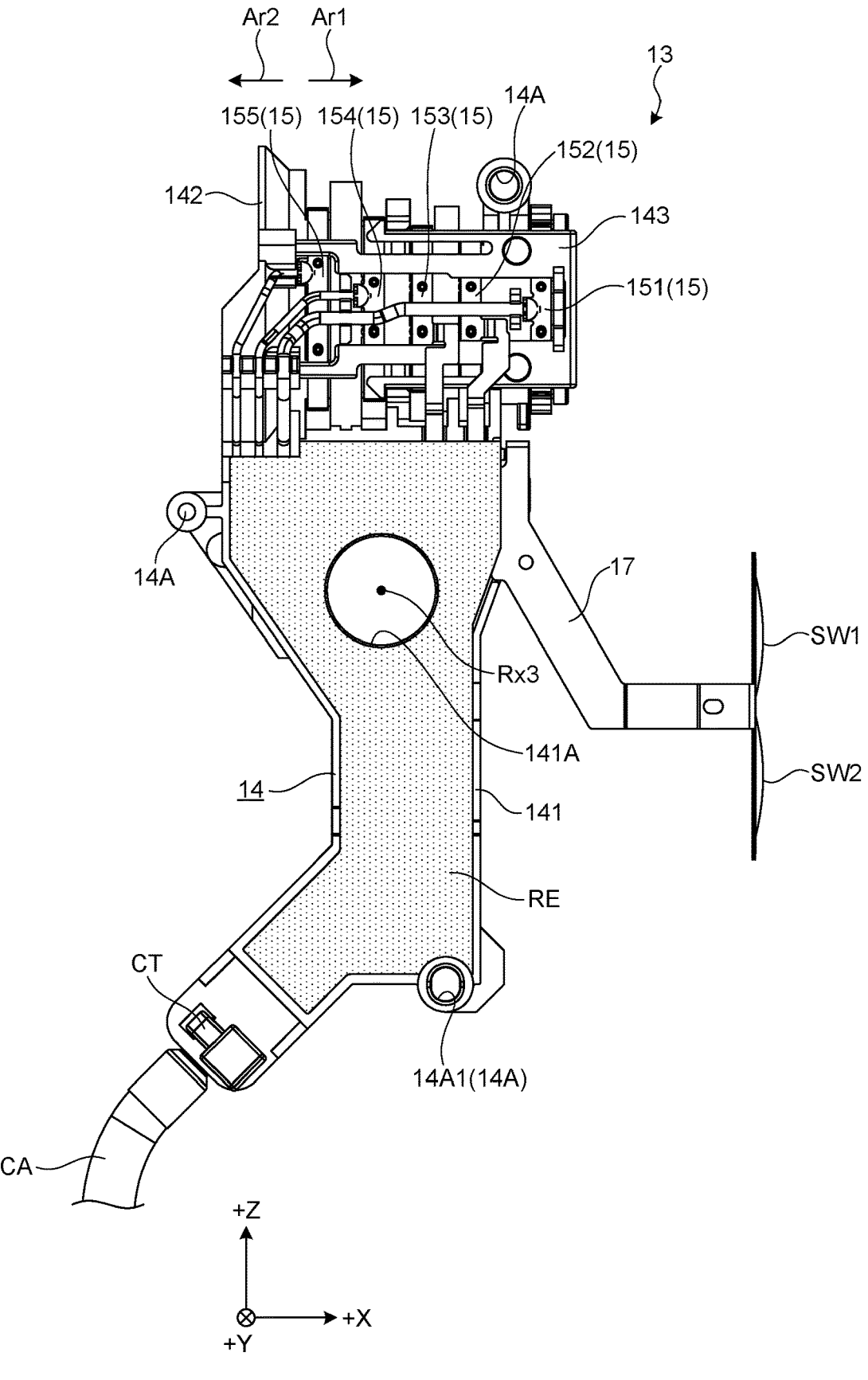
FIG. 9 is a diagram illustrating the overall configuration of the base unit.

A configuration of the base unit 13 will be described next. FIG. 8 and FIG. 9 are diagrams illustrating an overall configuration of the base unit 13. Specifically, FIG. 8 is a diagram of the base unit 13 as viewed from the positive direction along the Y-axis. FIG. 9 is a diagram of the base unit 13 as viewed from the negative direction along the Y-axis. For convenience of explanation, illustration of a switch supporting portion 18 and a metallic contact 19 has been omitted in FIG. 8. Furthermore, for convenience of explanation, resin RE is represented by dots in FIG. 9. The same applies to FIG. 22.

The base unit 13 includes, as illustrated in FIG. 8 or FIG. 9, a base member 14, a second terminal 15, a circuit board 16 (see FIG. 12), a flexible board 17, the switch supporting portion 18 (FIG. 5), and the metallic contact 19 (see FIG. 16) attached to the switch supporting portion 18. The circuit board 16 and flexible board 17 correspond to a substrate. Furthermore, the metallic contact 19 corresponds to a first contact.

The base member 14 is formed of a material that is electrically insulating and the base member 14 is fixed inside the holding case 6 by plural fixing portions 14A (FIG. 8 or FIG. 9), such as boss holes. This base member 14 includes, as illustrated in FIG. 8 or FIG. 9, a base member main body 141, the second terminal holding portion 142, and a terminal holding member 143 (FIG. 9).

The base member main body 141 is, as illustrated in FIG. 5, formed in a flat plate shape and arranged inside the holding case 6 in a posture where each plate surface of the base member main body 141 becomes parallel to the X-Z plane. Furthermore, the base member main body 141 extends, inside the holding case 6, up to the holding case main body 61 from an end portion of the fixed handle 62, the end portion being in a negative direction along the Z-axis.

A part of the cable CA is attached by a cable tie CT, the part being at one end of the cable CA, as illustrated in FIG. 8 or FIG. 9, to an end portion of the base member main body 141, the end portion being in the negative direction along the Z-axis. A part of the cable CA is laid outside the fixed handle 62 from a side surface of the fixed handle 62, the part being at the other end of the cable CA, the side surface being in the negative direction along the Z-axis. A part of the plural fixing portions 14A is provided, as illustrated in FIG. 8 or FIG. 9, at a position near the position at which the part at the one end of the cable CA is attached. Any load applied to the base unit 13 when the part at the other end of the cable CA is pulled would thereby be reduced. The cable CA may be configured to be attachable to and detachable from the base unit 13 via a connector.

Furthermore, a bearing hole 141A that penetrates through the base member main body 141, supports the switch supporting portion 18 rotatably about a third rotation axis Rx3 (a third rotation axis Rx3 orthogonal to the X-axis) parallel to the Y-axis, and is circular is formed in a part of the base member main body 141, the part being in the positive direction along the Z-axis. The third rotation axis Rx3 corresponds to "an axis intersecting an axis that is along a longitudinal axis". This third rotation axis Rx3 is not necessarily an axis orthogonal to the X-axis, as long as the third rotation axis Rx3 intersects the X-axis that is along the central axis Ax.

Figure 10:
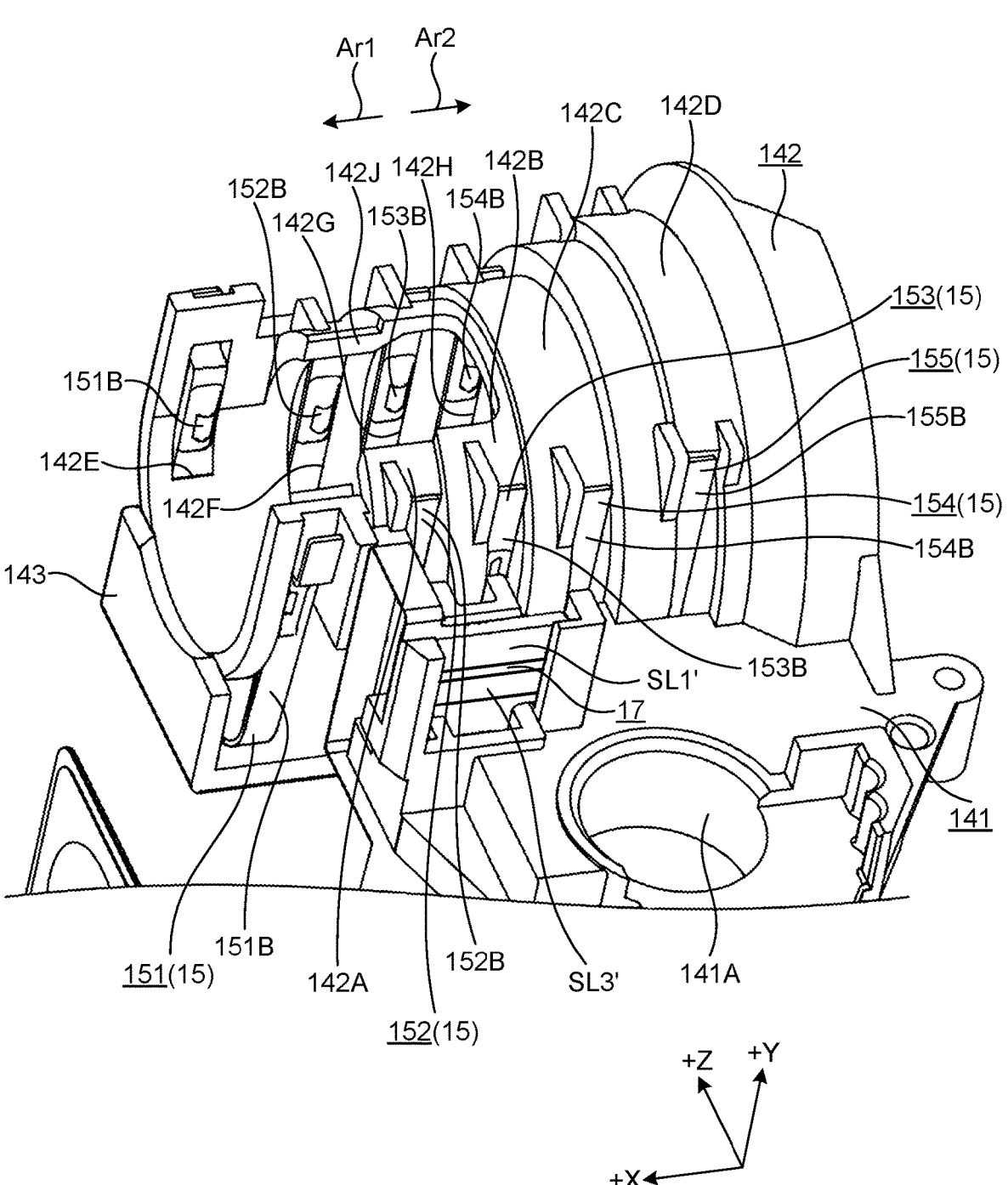
FIG. 10 is a diagram illustrating a configuration of a second terminal holding portion.
Figure 11:
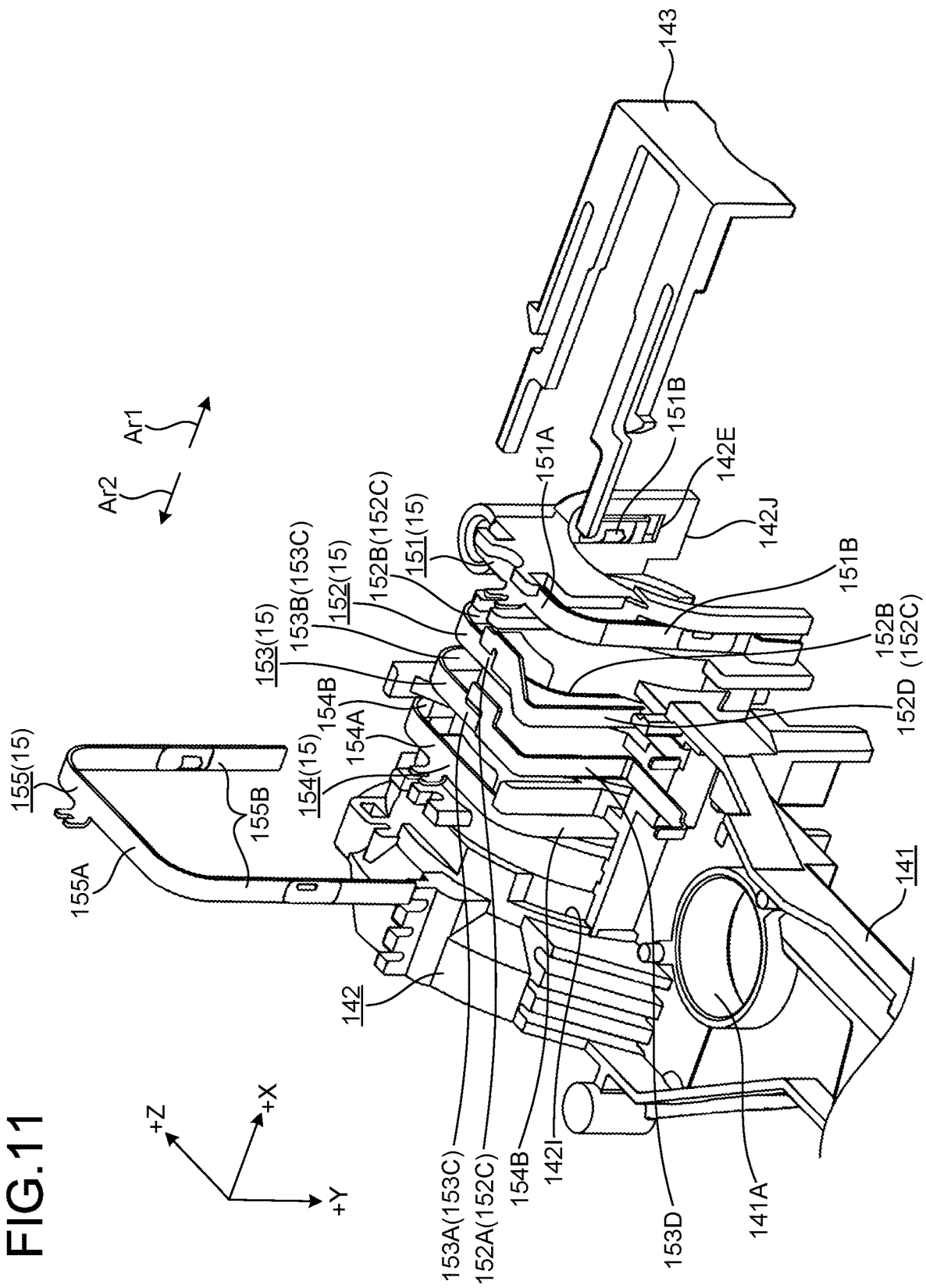
FIG. 11 is a diagram illustrating the configuration of the second terminal holding portion.

FIG. 10 and FIG. 11 are diagrams illustrating a configuration of the second terminal holding portion 142. Specifically, FIG. 10 is a perspective view of the second terminal holding portion 142 as viewed from the positive direction along the Y-axis. FIG. 11 is an exploded perspective view of the second terminal holding portion 142 and terminal holding member 143 as viewed from the negative direction along the Y-axis.

The second terminal holding portion 142 is a tubular body extending along the X-axis (the central axis Ax) as illustrated in FIG. 10 or FIG. 11, and is integrally formed with an end portion of the base member main body 141, the end portion being in the positive direction along the Z-axis. When the ultrasound transducer unit 5 is connected to the holding case main body 61, as illustrated in FIG. 3, FIG. 4, or FIG. 6, the first terminal holding portion 512 in the ultrasound transducer unit 5 is inserted through the second terminal holding portion 142.

An outer surface of this second terminal holding portion 142 is formed in a stepped shape having four steps 142A to 142D in order from the distal direction Ar1, as illustrated in FIG. 10. These four steps 142A to 142D each have a cross-sectional shape that is circular about the central axis Ax and increase in dimension of the diameter in the order of the four steps 142A to 142D. Furthermore, the dimensions of the inner diameters of these four steps 142A to 142D are set to be slightly larger than the dimensions of the outer diameters of the four steps 512A to 512D of the ultrasound transducer unit 5. In addition, a pair of openings 142E to 142I respectively penetrating through these four steps 142A to 142D along the Z-axis as illustrated in FIG. 10 or FIG. 11 are respectively formed in the four steps 142A to 142D.

Furthermore, a notched portion 142J is formed on a side surface of the second terminal holding portion 142, the side surface being in the positive direction along the Y-axis, the notched portion 142J being notched from an end portion of the second terminal holding portion 142, the end portion being in the distal direction Ar1, to a boundary between the steps 142B and 142C in the proximal direction Ar2, as illustrated in FIG. 10 or FIG. 11.

The terminal holding member 143 is a member to hold the second terminal 15 that is attached to an outer surface of the second terminal holding portion 142 and that is attached to each of the four steps 142A to 142D, the outer surface being in the negative direction along the Y-axis, as illustrated in FIG. 11. In this first embodiment, a snap fit is adopted as a structure for fixing the terminal holding member 143 to the second terminal holding portion 142.

The second terminal 15 includes, as illustrated in FIG. 10 or FIG. 11, the HF active electrode terminal 151, the HF return electrode terminal 152, the IR terminal 153, the US return electrode terminal 154, and the US active electrode terminal 155. Each of these terminals 151 to 155 is formed of an electrically conducting material.

The US active electrode terminal 155 includes a terminal base portion 155A and a pair of plate spring portions 155B, and is overall approximately U-shaped, as illustrated in FIG. 11.

The terminal base portion 155A has a flat plate shape extending along the Z-axis and is a portion fixed to an outer surface of the step 142D in a posture where each plate surface of the terminal base portion 155A becomes orthogonal to the Y-axis, the outer surface being in the negative direction along the Y-axis.

The pair of plate spring portions 155B are portions extending respectively from both ends of the terminal base portion 155A in the positive direction along the Y-axis and are configured to be elastically deformable along the Z-axis with the both ends respectively being pivot points. Furthermore, in a state where the terminal base portion 155A has been fixed to the step 142D, parts of the pair of plate spring portions 155B are respectively exposed to the interior of the second terminal holding portion 142, through the pair of openings 142I. The US active electrode terminal 155 (the pair of plate spring portions 155B) is electrically connected to the US active electrode terminal 524 by coming into contact with the US active electrode terminal 524 in the ultrasound transducer unit 5 when the ultrasound transducer unit 5 is connected to the holding case main body 61.

Figure 21:
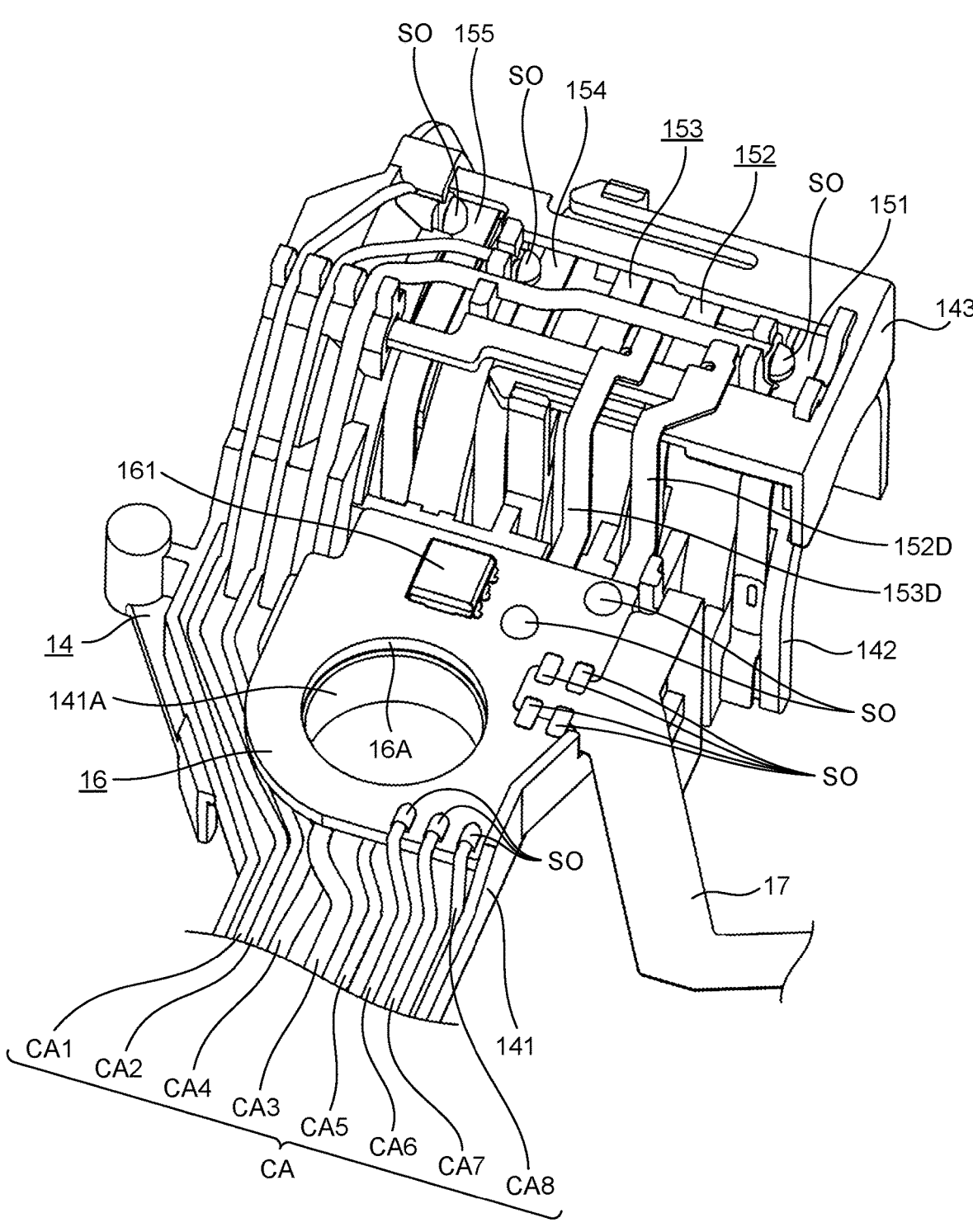
FIG. 21 is a diagram illustrating the method of manufacturing the energy treatment tool.

The cable CA is formed of eight cables that are a US active electrode cable CA1, a US return electrode cable CA2, an HF return electrode cable CA3, an HF active electrode cable CA4, a memory cable CA5, and first to third switch cables CA6 to CA8 (see FIG. 21). The electric cable C0 is similarly formed of eight cables.

The US active electrode cable CA1 and the US return electrode cable CA2 serve as electric paths for drive signals supplied from the control device 3 via the electric cable C0. The US active electrode cable CA1 is electrically connected directly to the US active electrode terminal 155 (see FIG. 21).

The HF return electrode cable CA3 and the HF active electrode cable CA4 serve as electric paths for high frequency signals supplied from the control device 3 via the electric cable C0.

The memory cable CA5 is an electric path used in communication between: the control device 3; and the built-in TD memory (not illustrated in the drawings) in the ultrasound transducer unit 5, and the handpiece memory 161 (see FIG. 12) mounted on the circuit board 16.

The first to third switch cables CA6 to CA8 are cables electrically connecting the electric cable C0 respectively to the first to third switch elements SW1 to SW3.

The US return electrode terminal 154 includes a terminal base portion 154A and a pair of plate spring portions 154B and is overall approximately U-shaped, as illustrated in FIG. 10 or FIG. 11.

The terminal base portion 154A has a flat plate shape having a longitudinal length shorter than that of the terminal base portion 155A, correspondingly to the dimension of the outer diameter of the step 142C. The terminal base portion 154A is fixed to an outer surface of the step 142C, the outer surface being in the negative direction along the Y-axis, in a posture where each plate surface of the terminal base portion 154A is orthogonal to the Y-axis.

The pair of plate spring portions 154B correspond to portions extending respectively from both ends of the terminal base portion 154A in the positive direction along the Y-axis and are configured to be elastically deformable along the Z-axis with the both ends being pivot points. Each of these pair of plate spring portions 154B has the same shape as the plate spring portion 155B. Furthermore, in a state where the terminal base portion 154A has been fixed to the step 142C, parts of the pair of plate spring portions 154B are respectively exposed to the interior of the second terminal holding portion 142, through the pair of openings 142H. The US return electrode terminal 154 (the pair of plate spring portions 154B) is electrically connected to the US return electrode terminal 523 by coming into contact with the US return electrode terminal 523 in the ultrasound transducer unit 5 when the ultrasound transducer unit 5 is connected to the holding case main body 61.

The US return electrode cable CA2 is electrically connected directly to the US return electrode terminal 154 (see FIG. 21).

The IR terminal 153 includes a terminal base portion 153A and a pair of plate spring portions 153B, and includes an IR terminal main body 153C (FIG. 11) that is overall approximately U-shaped, and an extending portion 153D (FIG. 11) that is integrally formed with the IR terminal main body 153C and that extends in the negative direction along the Z-axis from the terminal base portion 153A, as illustrated in FIG. 10 or FIG. 11.

The terminal base portion 153A has a flat plate shape having a longitudinal length shorter than that of the terminal base portion 154A, correspondingly to the dimension of the outer diameter of the step 142B. The terminal base portion 153A is fixed to an outer surface of the step 142B, the outer surface being in the negative direction along the Y-axis, in a posture where each plate surface of the terminal base portion 153A is orthogonal to the Y-axis.

The pair of plate spring portions 153B are portions extending respectively from both ends of the terminal base portion 153A in the positive direction along the Y-axis and are configured to be elastically deformable along the Z-axis with the both ends being pivot points. Each of these pair of plate spring portions 153B has the same shape as the plate spring portion 155B. Furthermore, in a state where the terminal base portion 153A has been fixed to the step 142B, parts of the pair of plate spring portions 153B are respectively exposed to the interior of the second terminal holding portion 142, through the pair of openings 142G. The IR terminal 153 (the pair of plate spring portions 153B) is electrically connected to the IR terminal 522 by coming into contact with the IR terminal 522 in the ultrasound transducer unit 5 when the ultrasound transducer unit 5 is connected to the holding case main body 61.

The HF return electrode terminal 152 includes a terminal base portion 152A and a pair of plate spring portions 152B, and includes an HF return electrode terminal main body 152C (FIG. 11) that is overall approximately U-shaped and an extending portion 152D (FIG. 11) that is integrally formed with the HF return electrode terminal main body 152C and extends from the terminal base portion 152A in the negative direction along the Z-axis, as illustrated in FIG. 10 or FIG. 11.

The terminal base portion 152A has a flat plate shape having a longitudinal length shorter than that of the terminal base portion 153A, correspondingly to the dimension of the outer diameter of the step 142A. The terminal base portion 152A is fixed to a part of an outer surface of the step 142A in a posture where each plate surface of the terminal base portion 152A is orthogonal to the Y-axis, the part being in the proximal direction Ar2, the outer surface being in the negative direction along the Y-axis.

The pair of plate spring portions 152B are portions extending respectively from both ends of the terminal base portion 152A in the positive direction along the Y-axis and are configured to be elastically deformable along the Z-axis with the both ends being pivot points. Each of these pair of plate spring portions 152B has the same shape as the plate spring portion 155B. Furthermore, in a state where the terminal base portion 152A has been fixed to the step 142A, portions of the pair of plate spring portions 152B are respectively exposed to the interior of the second terminal holding portion 142, through the pair of openings 142F. The HF return electrode terminal 152 (the pair of plate spring portions 152B) is electrically connected to the HF return electrode terminal 521 by coming into contact with the HF return electrode terminal 521 in the ultrasound transducer unit 5 when the ultrasound transducer unit 5 is connected to the holding case main body 61.

The HF active electrode terminal 151 includes a terminal base portion 151A and a pair of plate spring portions 151B and is overall approximately U-shaped, as illustrated in FIG. 10 or FIG. 11.

The terminal base portion 151A has the same shape as the terminal base portion 152A. The terminal base portion 151A is fixed to a part of the outer surface of the step 142A in a posture where each plate surface of the terminal base portion 151A is orthogonal to the Y-axis, the part being in the distal direction Ar1, the outer surface being in the negative direction along the Y-axis.

The pair of plate spring portions 151B are portions extending respectively from both ends of the terminal base portion 151A in the positive direction along the Y-axis and are configured to be elastically deformable along the Z-axis with the both ends being pivot points. Each of these pair of plate spring portions 151B has the same shape as the plate spring portion 155B. Furthermore, in a state where the terminal base portion 151A has been fixed to the step 142A, portions of the pair of plate spring portions 151B are respectively exposed to the interior of the second terminal holding portion 142, through the pair of openings 142E. The HF active electrode terminal 151 (the pair of plate spring portions 151B) is electrically connected to the HF active electrode terminal 103A by coming into contact with the HF active electrode terminal 103A provided in the probe holder 103.

The HF active electrode cable CA4 is electrically connected directly to the HF active electrode terminal 151 (see FIG. 21).

As described above, all of the plate spring portions 151B, 152B, 153B, 154B, and 155B in the terminals 151 to 155 have the same shape. Therefore, contact pressure from the terminals 151 to 155 on the terminals 103A and 521 to 524 are all able to be set the same.

Figure 12:
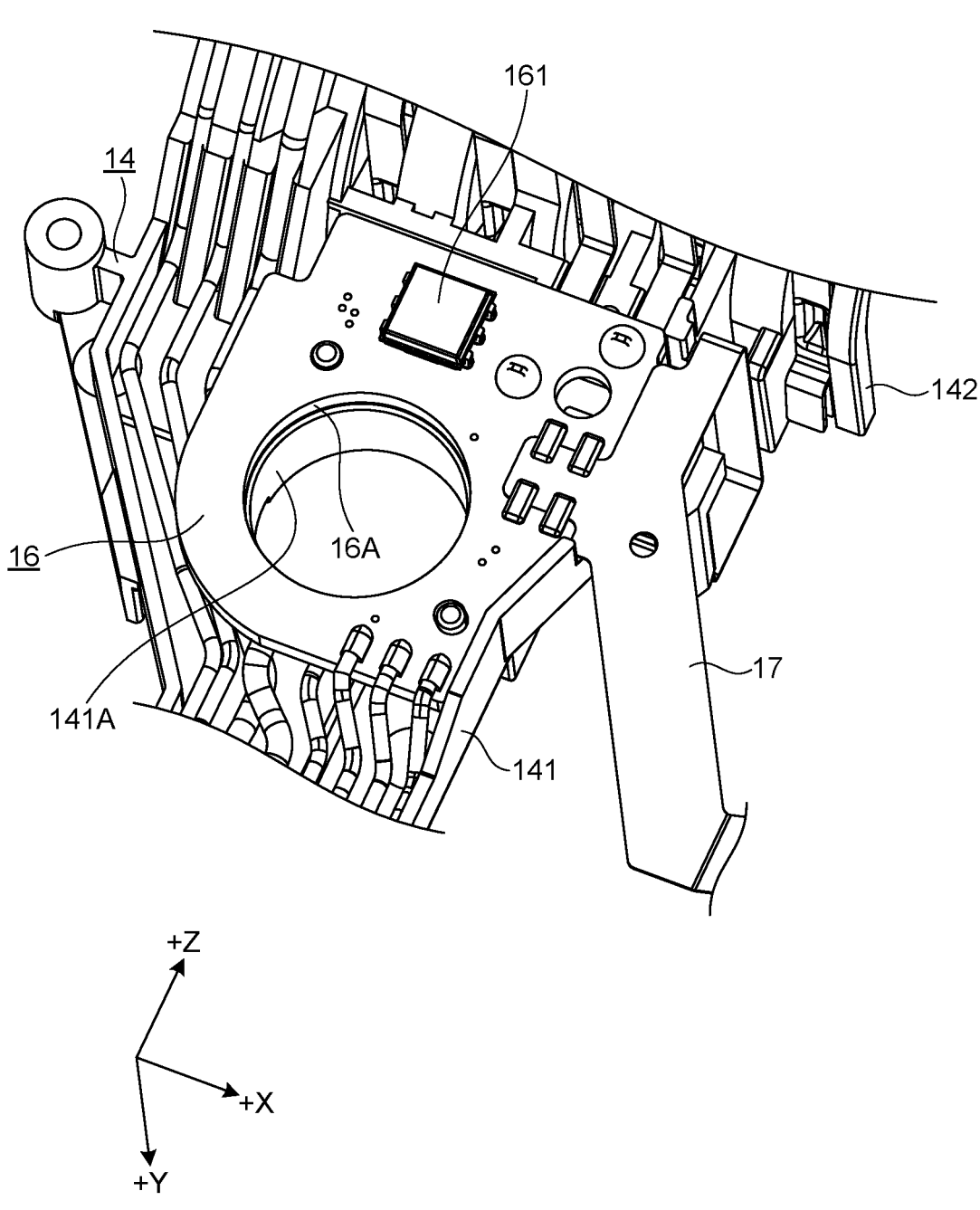
FIG. 12 is a diagram illustrating a circuit board.

FIG. 12 is a diagram illustrating the circuit board 16. Specifically, FIG. 12 is a diagram in which an arrangement position of the circuit board 16 in the base unit 13 is viewed from the negative direction along the Y-axis.

The circuit board 16 is arranged at a position facing the bearing hole 141A, the position being on a plate surface of the base member main body 141, the plate surface being in the negative direction along the Y-axis, as illustrated in FIG. 12. A through hole 16A penetrating through the circuit board 16 and communicated with the bearing hole 141A is formed in this circuit board 16. Furthermore, plural electric wirings including first to third electric wirings SL1 to SL3 (see FIG. 13), the handpiece memory 161 (FIG. 12), and first to third diodes 162 to 164 (see FIG. 20) are mounted on the circuit board 16.

Figure 13:
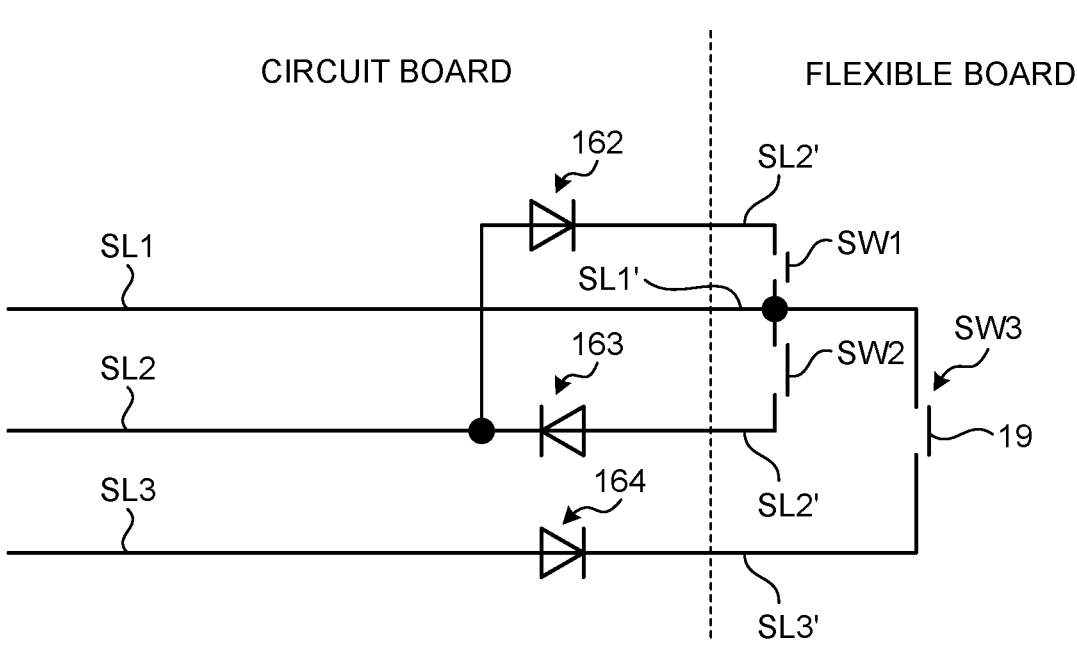
FIG. 13 is a circuit diagram for detection of operations on a first switch, a second switch, and a third switch.

The first electric wiring SL1 is electrically connected to each of the first to third switch elements SW1 to SW3 via a first electric wiring SL1' mounted on the flexible board 17 (see FIG. 13).

The second electric wiring SL2 is electrically connected to each of the first and second diodes 162 and 163, and is electrically connected to each of the first and second switch elements SW1 and SW2 via a second electric wiring SL2' mounted on the flexible board 17 (see FIG. 13).

The third electric wiring SL3 is electrically connected to the third diode 164 and is electrically connected to the third switch SW3 via a third electric wiring SL3' mounted on the flexible board 17 (see FIG. 13).

The first to third switch cables CA6 to CA8 are each connected to the circuit board 16. The first to third electric wirings SL1 to SL3 are thereby electrically connected respectively to the first to third switch cables CA6 to CA8.

The handpiece memory 161 stores, for example, the identification information identifying the handpiece 4. The extending portion 153D in the IR terminal 153, the extending portion 152D in the HF return electrode terminal 152, the memory cable CA5, and the HF return electrode cable CA3 are each connected to the circuit board 16. The handpiece memory 161 is thereby electrically connected, via a pair of electric wirings (not illustrated in the drawings) mounted on the circuit board 16, to each of the memory cable CA5 functioning as a signal line used in communication with the control device 3 and the HF return electrode cable CA3 functioning as a ground line used in communication with the control device 3. The handpiece memory 161 is also electrically connected to each of the IR terminal 153 and the HF return electrode terminal 152, via the pair of electric wirings. That is, similarly to the handpiece memory 161, the built-in TD memory (not illustrated in the drawings) in the ultrasound transducer unit 5 is electrically connected to each of the memory cable CA5 and the HF return electrode cable CA3.

The flexible board 17 is connected to the circuit board 16 and extends from the position where the flexible board 17 is connected to the circuit board 16 to each of: positions where the first and second switches 8A and 8B are arranged; and a position where the metallic contact 19 (see FIG. 16 or FIG. 17) attached to the switch supporting portion 18 is arranged. The first to third electric wirings SL1' to SL3' and the first and second switch elements SW1 and SW2 are mounted on this flexible board 17.

The first electric wiring SL1' is a wiring that relays between the first electric wiring SL1 and the first to third switch elements SW1 to SW3 (see FIG. 13).

The second electric wiring SL2' is a wiring that relays between the second electric wiring SL2 and the first and second switch elements SW1 and SW2 (see FIG. 13).

The third electric wiring SL3' is a wiring that relays between the third electric wiring SL3 and the third switch element SW3 (see FIG. 13).

A part of the first electric wiring SL1' and a part of the third electric wiring SL3' are exposed to the outside of the flexible board 17, at a position facing the metallic contact 19. The part of the first electric wiring SL1', the part of the third electric wiring SL3', and the metallic contact 19 form the third switch element SW3. The first and third electric wirings SL1' and SL3' correspond to a wiring pattern.

The first switch element SW1 is provided at a position (FIG. 5) facing the first switch 8A and detects any first energy output mode setting operation on the first switch 8A.

The second switch element SW2 is provided at a position (FIG. 5) facing the second switch 8B and detects any second energy output mode setting operation on the second switch 8B.

FIG. 13 is a circuit diagram for detection of operations on the first to third switches 8A to 8C.

The control device 3 recognizes that operations have been performed on the first to third switches 8A to 8C, as described below.

If a first energy output mode setting operation has been performed on the first switch 8A, the first and second electric wirings SL1' and SL2' are electrically connected to each other by the first switch element SW1. Electric current then flows, by means of the first to third diodes 162 to 164, only in a direction from the second switch cable CA7 (the second electric wirings SL2 and SL2') to the first switch cable CA6 (the first electric wirings SL1 and SL1'). By recognizing this flow of electric current, the control device 3 recognizes that a first energy output mode setting operation has been performed on the first switch 8A.

If a second energy output mode setting operation has been performed on the second switch 8B, the first and second electric wirings SL1' and SL2' are electrically connected to each other by the second switch element SW2. Electric current then flows, by means of the first to third diodes 162 to 164, only in a direction from the first switch cable CA6 (the first electric wirings SL1 and SL1') to the second switch cable CA7 (the second electric wirings SL2 and SL2'). By recognizing this flow of electric current, the control device 3 recognizes that a second energy output mode setting operation has been performed on the second switch 8B.

If a changing operation has been performed on the third switch 8C, the first and third electric wirings SL1' and SL3' are brought into an electrically connected state where the first and third electric wirings SL1' and SL3' are electrically connected to each other or an electrically disconnected state where the first and third electric wirings SL1' and SL3' are electrically disconnected to each other by the third switch element SW3. Electric current then flows, by means of the first to third diodes 162 to 164, only in a direction from the third switch cable CA8 (the third electric wirings SL3 and SL3') to the first switch cable CA6 (the first electric wirings SL1 and SL1') in this electrically connected state. By recognizing this flow of electric current, the control device 3 recognizes whether or not a changing operation has been performed on the third switch 8C. The control device 3 performs switching to one of the high output mode and the low output mode, in a state (a contact state) where the first and third electric wirings SL1' and SL3' are electrically connected to each other. Furthermore, the control device 3 performs switching to the other one of the high output mode and the low output mode, in a state (a noncontact state) where the first and third electric wirings SL1' and SL3' are electrically disconnected to each other. That is, the output state of energy to be applied to a target site is set such that output states in the contact state and the noncontact state differ from each other.

Figure 14:
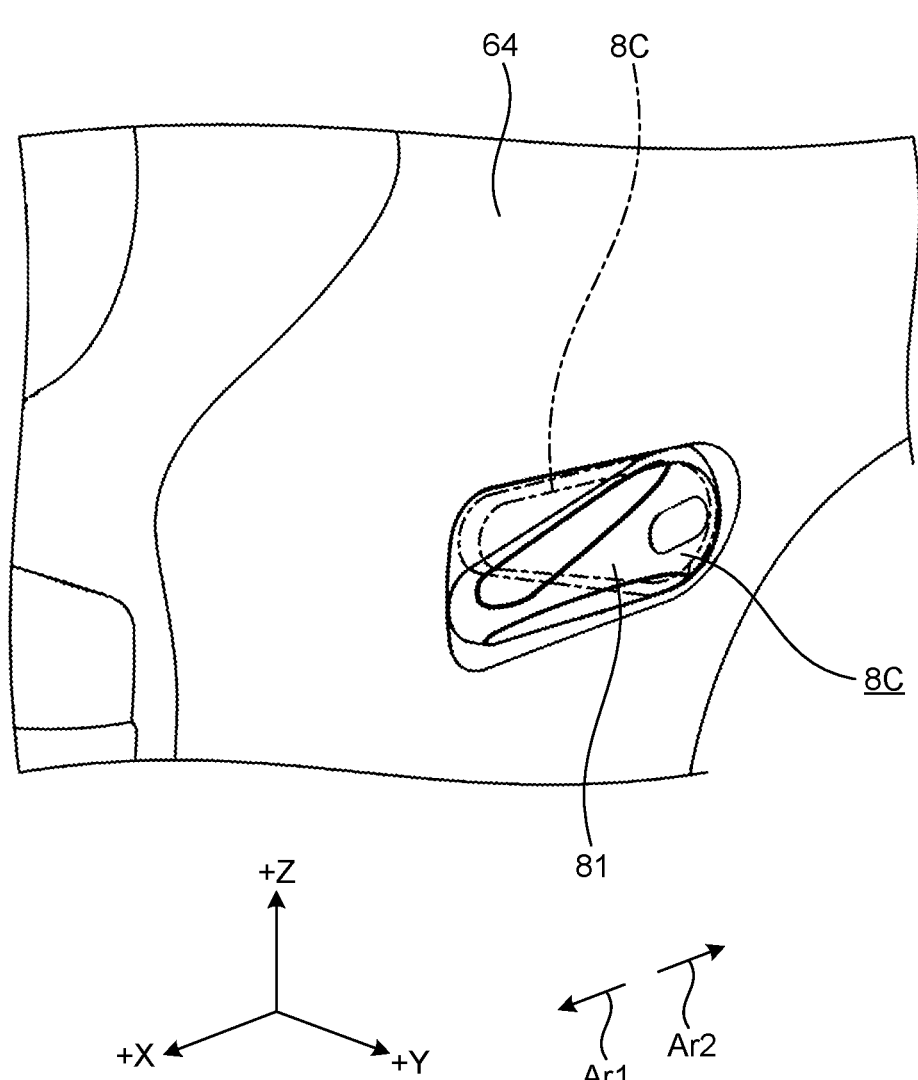
FIG. 14 is a diagram illustrating a support structure of the third switch.
Figure 15:
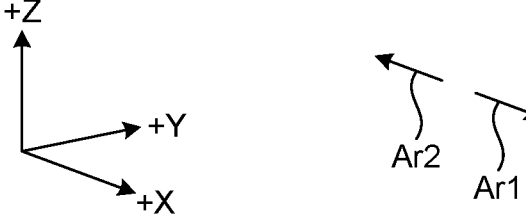
FIG. 15 is a diagram illustrating the support structure of the third switch.
Figure 16:
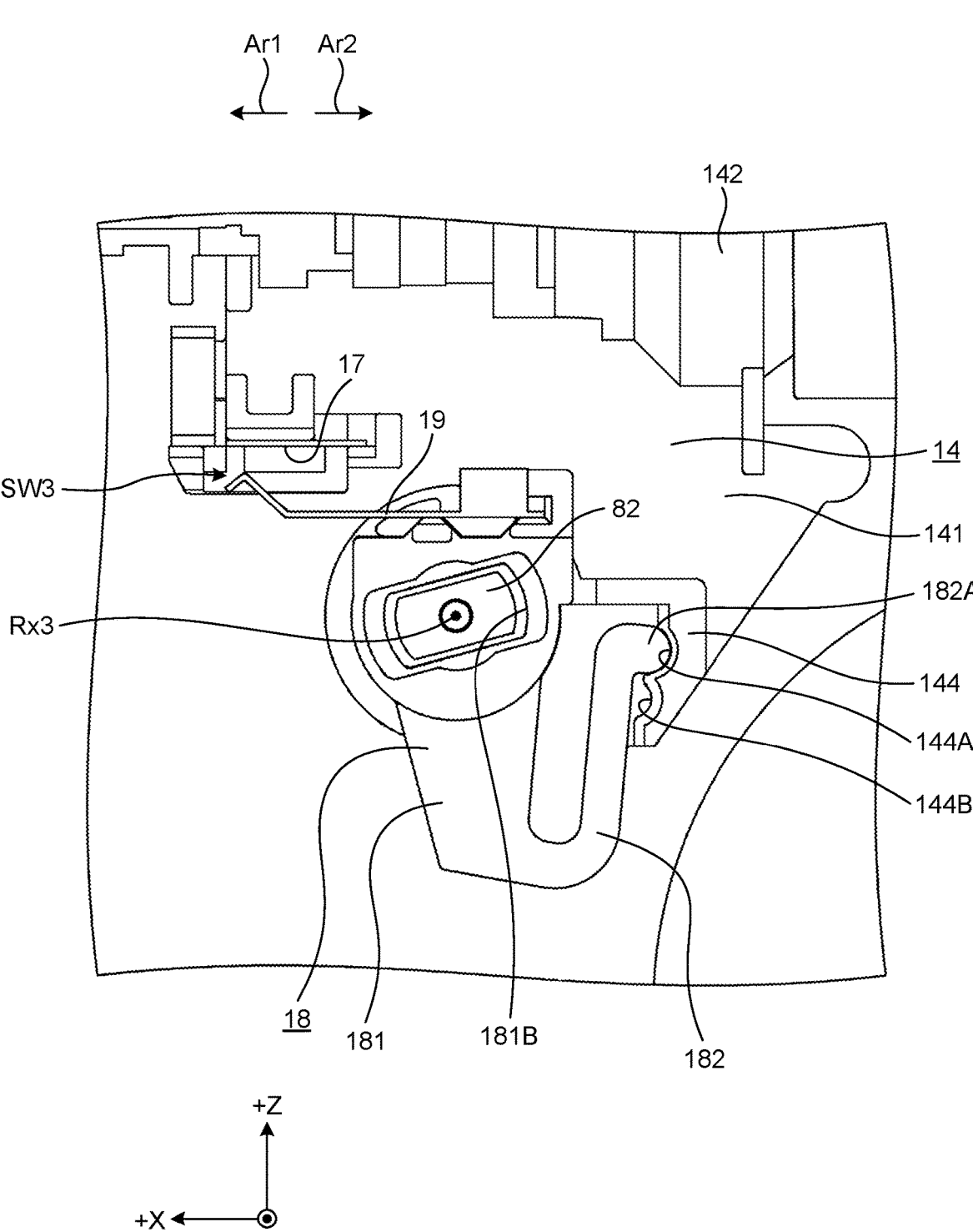
FIG. 16 is a diagram illustrating the support structure of the third switch.
Figure 17:
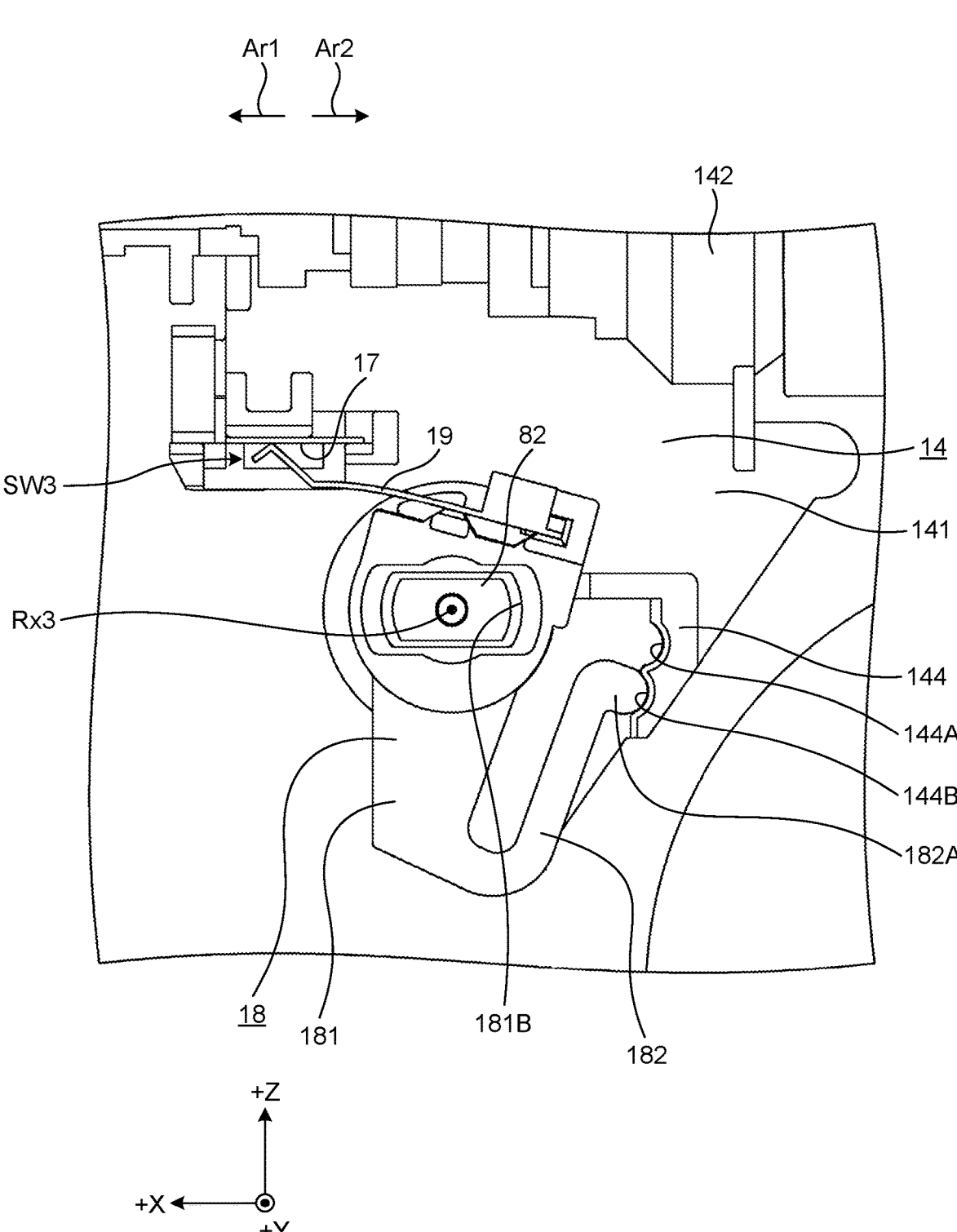
FIG. 17 is a diagram illustrating the support structure of the third switch.

FIGS. 14 to 17 are diagrams illustrating a support structure of the third switches 8C. Specifically, FIG. 14 is a diagram of the holding case 6 as viewed from the positive direction along the Y-axis. FIG. 15 is a diagram of the holding case 6 as viewed from the negative direction along the Y-axis. FIG. 16 and FIG. 17 are diagrams of the switch supporting portion 18 as viewed from the positive direction along the Y-axis.

A structure of the third switches 8C will be described before description of a configuration of the switch supporting portion 18.

The pair of third switches 8C have the same shape. The third switches 8C each include a pinched portion 81 and a shaft portion 82, as illustrated in FIG. 5 or FIG. 14 to FIG. 17.

The pinched portion 81 is a portion that receives a changing operation by an operator, such as a surgeon. In this first embodiment, the pinched portion 81 has a tapered shape that is tapered in the distal direction Ar1.

The shaft portion 82 protrudes along the Y-axis from a part of the pinched portion 81, the part being in the proximal direction Ar2. In this first embodiment, the shaft portion 82 has a rectangular cross-sectional shape. The shaft portion 82 of one of the pair of third switches 8C, the one being in the positive direction along the Y-axis, is inserted through a round hole 641 (FIG. 5) penetrating through the second housing 64 and protrudes to the interior of the holding case 6. The shaft portion 82 of the third switch 8C in the negative direction along the Y-axis is inserted through a round hole (not illustrated in the drawings) penetrating through the first housing 63 and protrudes to the interior of the holding case 6.

The switch supporting portion 18 corresponds to a driver. This switch supporting portion 18 is formed of a material that is electrically insulating, and is arranged, as illustrated in FIG. 5, FIG. 16, or FIG. 17, at a position facing the bearing hole 141A, on a plate surface of the base member main body 141, the plate surface being in the positive direction along the Y-axis. The switch supporting portion 18 includes a supporting portion main body 181 and a spring portion 182.

The supporting portion main body 181 includes, as illustrated in FIG. 5, a columnar shaft 181A that extends along the Y-axis, that is inserted through the bearing hole 141A, and that is cylindrical. The dimension of the outer diameter of this columnar shaft 181A is set slightly smaller than the dimension of the inner diameter of the bearing hole 141A. The columnar shaft 181A is pivotally supported by the bearing hole 141A and the switch supporting portion 18 is rotatable about the third rotation axis Rx3.

Furthermore, a fitting hole 181B (FIG. 5, FIG. 16, or FIG. 17) where each shaft portion 82 of the pair of third switches 8C is fitted is formed in the columnar shaft 181A, the fitting hole 181B penetrating through the columnar shaft 181A along the Y-axis and having a rectangular cross-sectional shape, each of the shaft portions 82 protruding to the interior of the holding case 6. That is, the pair of third switches 8C are supported rotatably about the third rotation axis Rx3, at a central position in the interior of the holding case 6 along the Y-axis, by the bearing hole 141A and the columnar shaft 181A.

The spring portion 182 is a portion protruding from an end portion of the supporting portion main body 181 and extending by bending in the positive direction along the Z-axis, the end portion being in the negative direction along the Z-axis, and is configured to be elastically deformable along the X-axis with the end portion of the supporting portion main body 181 being a pivot point, the end portion being in the negative direction along the Z-axis, as illustrated in FIG. 16 or FIG. 17. Furthermore, a protruding portion 182A protruding in the proximal direction Ar2 is provided at an end portion of the spring portion 182, the end portion being in the positive direction along the Z-axis.

An engagement projection 144 protruding in the positive direction along the Y-axis from a position in the base member main body 141 is formed on the plate surface of the base member main body 141, the plate surface being in the positive direction along the Y-axis, the position being in the proximal direction Ar2 relatively to the switch supporting portion 18, as illustrated in FIG. 16 or FIG. 17. Furthermore, first and second engagement recessed portions 144A and 144B corresponding to the shape of the protruding portion 182A of the spring portion 182 are provided side by side in a direction along the Z-axis on a side surface of the engagement projection 144, the side surface being in the distal direction Ar1.

The metallic contact 19 is attached to an end portion of the switch supporting portion 18, as illustrated in FIG. 16 or FIG. 17, the end portion being in the positive direction along the Z-axis. The metallic contact 19 forms the third switch element SW3. That is, when the metallic contact 19 comes into contact (being in a contact state) with parts (FIG. 10) of the first and third electric wirings SL1' and SL3', the parts being exposed to the outside of the flexible board 17, the first and third electric wirings SL1' and SL3' are electrically connected to each other. Furthermore, when the metallic contact 19 separates from (being brought into a noncontact state with) the parts of the first and third electric wirings SL1' and SL3', the first and third electric wirings SL1' and SL3' are brought into a state where the first and third electric wirings SL1' and SL3' are electrically disconnected to each other.

When a portion of the third switch 8C is moved in the negative direction along the Z-axis (see the third switch 8C illustrated with a solid line in FIG. 14 or FIG. 15), the portion being in the distal direction Ar1, the switch supporting portion 18 is rotated anticlockwise in FIG. 16 about the third rotation axis Rx and brought into a state (a first state) illustrated in FIG. 16. When this happens, the metallic contact 19 separates from the parts of the first and third electric wirings SL1' and SL3', the parts being exposed to the outside of the flexible board 17. That is, the first and third electric wirings SL1' and SL3' are brought into a state where the first and third electric wirings SL1' and SL3' are electrically disconnected to each other.

On the contrary, when the portion of the third switch 8C is moved in the positive direction along the Z-axis (see the third switch 8C illustrated with a dash-dotted line in FIG. 14 or FIG. 15), the portion being in the distal direction Ar1, the switch supporting portion 18 is rotated clockwise in FIG. 17 about the third rotation axis Rx3 and brought into a state (a second state) illustrated in FIG. 17. When this happens, the metallic contact 19 comes into contact with each of the parts of the first and third electric wirings SL1' and SL3', the parts being exposed to the outside of the flexible board 17. That is, the first and third electric wirings SL1' and SL3 are electrically connected to each other.

In both of the case where the portion of the third switch 8C is moved in the negative direction along the Z-axis, the portion being in the distal direction Ar1, and the case where the portion of the third switch 8C is moved in the positive direction along the Z-axis, the portion being in the distal direction Ar1, the spring portion 182 slides on the side surface of the engagement projection 144 while being elastically deformed along the X-axis, the side surface being in the distal direction Ar1. When the portion of the third switch 8C is moved in the negative direction along the Z-axis, the portion being in the distal direction Ar1 (in the case of the first state), the protruding portion 182A engages with the first engagement recessed portion 144A positioned in the positive direction along the Z-axis (FIG. 16). The first state is thereby maintained. Furthermore, when the portion of the third switch 8C is moved in the positive direction along the Z-axis, the portion being in the distal direction Ar1 (in the case of the second state), the protruding portion 182A engages with the second engagement recessed portion 144B positioned in the negative direction along the Z-axis (FIG. 17). The second state is thereby maintained. According to the engagement of the protruding portion 182A with the first or second engagement recessed portion 144A or 144B, the spring portion 182 provides vibration to the pair of third switches 8C. By being configured like this, the third switch 8C is able to be prevented from being switched erroneously even if, for example, a finger of an operator unintentionally touches the third switch 8C, while enabling switching operations to be easily performed without application of excessive force. In addition, because the pair of third switches 8C move in association with each other, the pair of third switches 8C are able to be operated by either a right-hander or a left-hander, and by visually recognizing the position of the portion in the distal direction Ar1, the operator is able to readily confirm which mode the pair of third switches 8C are in.

Method of Manufacturing Energy Treatment Tool

A method of manufacturing the energy treatment tool 2 described above will be described next.

Figure 18:
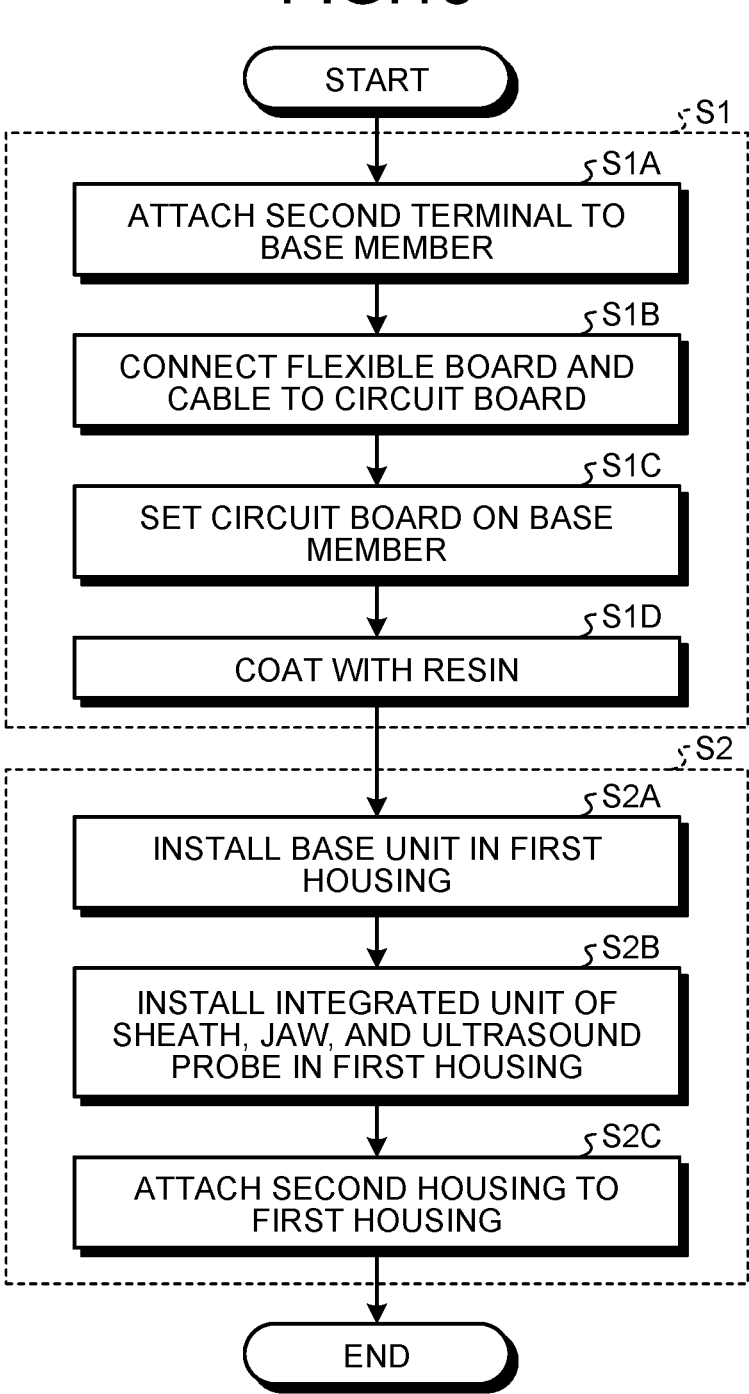
FIG. 18 is a flowchart illustrating a method of manufacturing the energy treatment tool.

FIG. 18 is a flowchart illustrating a method of manufacturing the energy treatment tool 2. FIG. 19 to FIG. 22 are diagrams illustrating the method of manufacturing the energy treatment tool 2.

Steps S1 and S2 described below are performed at difference places. Specifically, Step S2 is performed at a place (hereinafter, referred to as a second place), such as a clean room, that is comparatively high in cleanliness (cleanness). On the contrary, Step S1 is performed at a place (hereinafter, referred to as a first place), such as a clean room, that is lower in cleanliness (cleanness) than the second place.

Steps S1 and S2 will be described below in this order.

Step S1

At Step S1, an operator assembles the base unit 13 at the first place, as described below.

The operator attaches the second terminal 15 to the base member 14, as illustrated in FIG. 11 (Step S1A).

Figure 19:
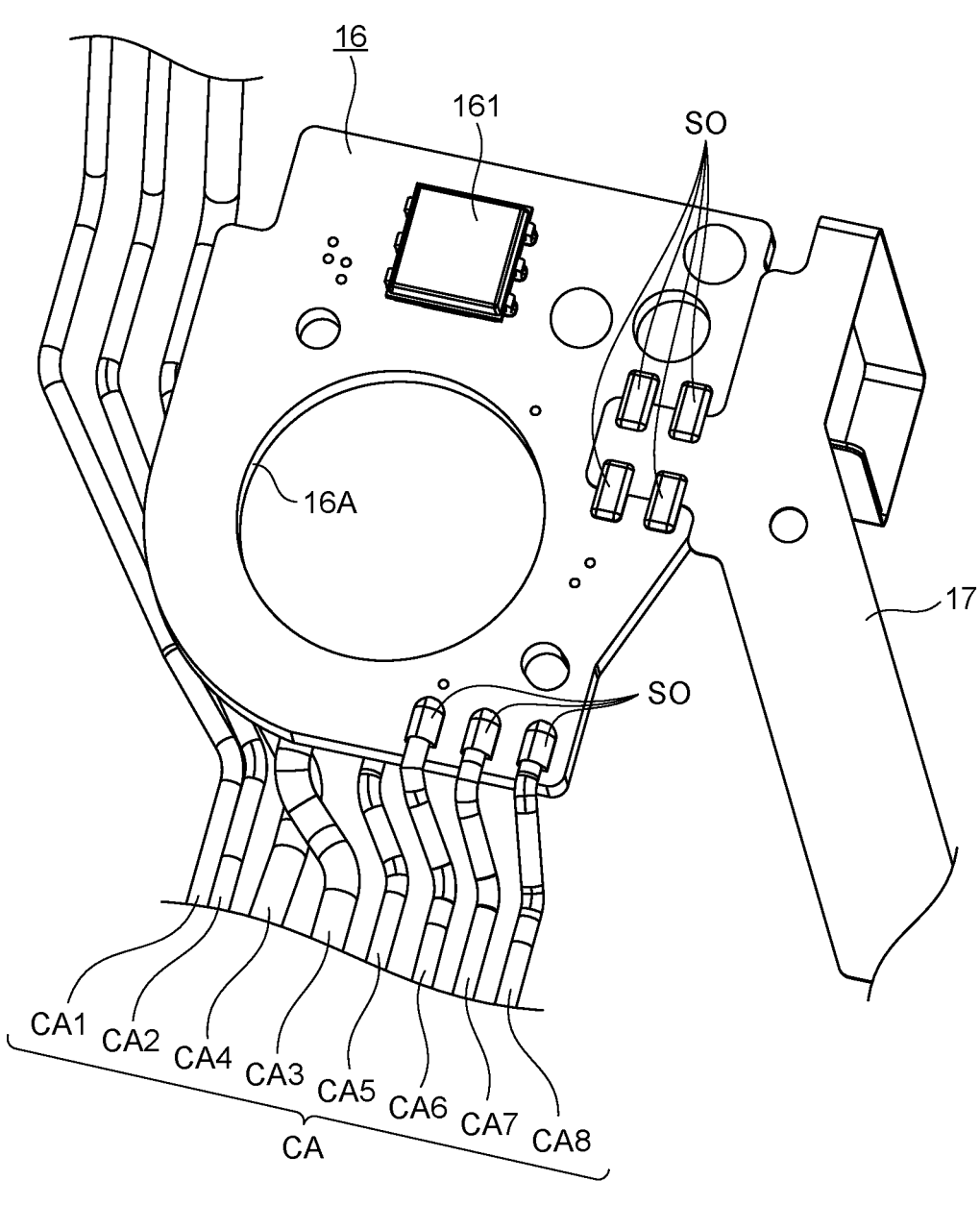
FIG. 19 is a diagram illustrating the method of manufacturing the energy treatment tool.
Figure 20:
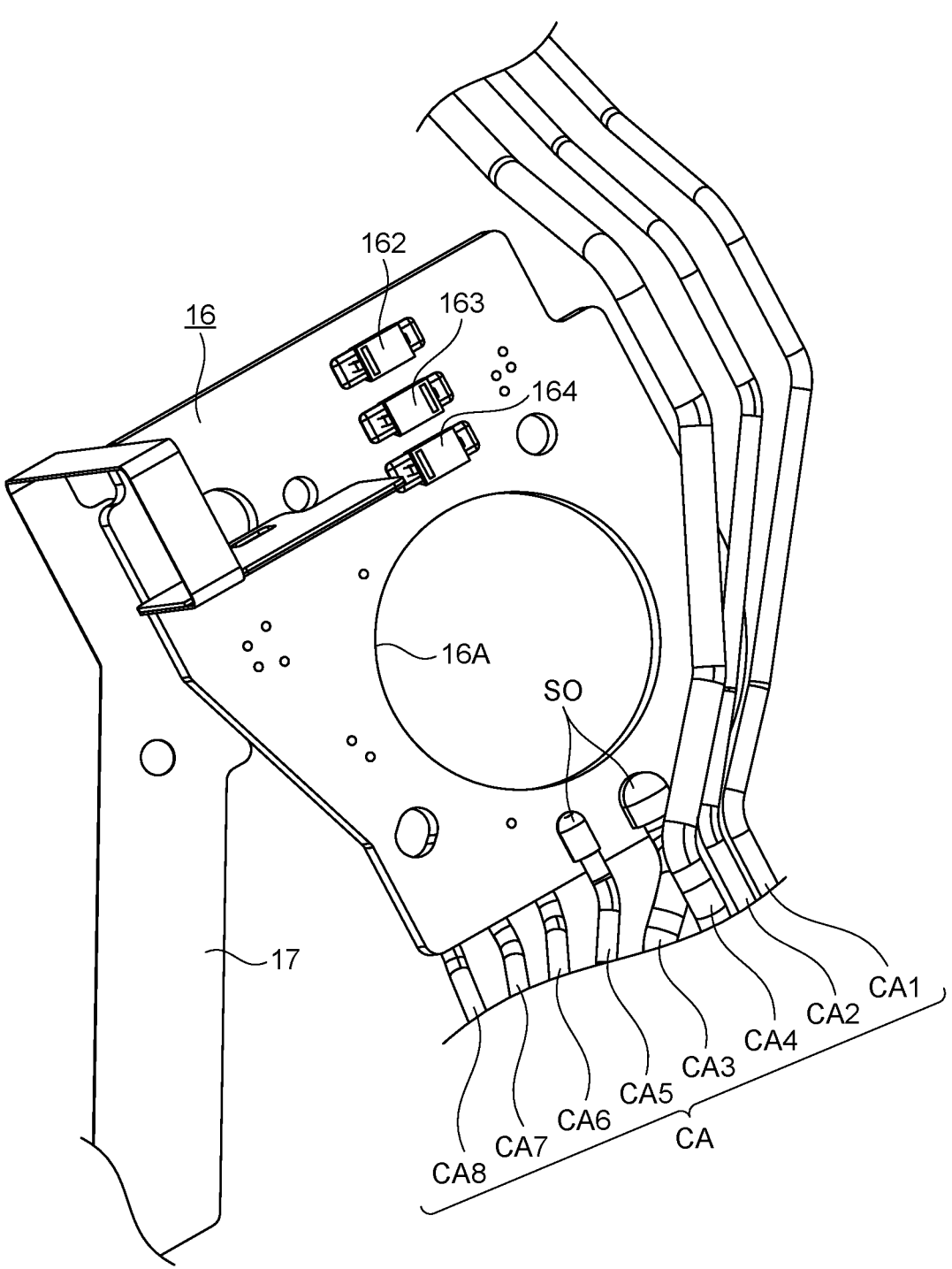
FIG. 20 is a diagram illustrating the method of manufacturing the energy treatment tool.

After Step S1A, the operator connects each of the flexible board 17 and the cables CA3 and CA5 to CA8 to the circuit board 16, using solder SO, as illustrated in FIG. 19 and FIG. 20 (Step S1B).

After Step S1B, the operator sets the circuit board 16 relatively to the base member 14, as described below (Step S1C).

Specifically, the operator fixes the cable CA to the base member 14, using the cable tie CT. Furthermore, as illustrated in FIG. 21, the operator connects the cables CA4, CA2, and CA1, respectively to the terminals 151, 154, and 155, using solder SO. In addition, the operator connects each of the extending portions 152D and 153D of the terminals 152 and 153 to the circuit board 16, using solder SO.

Figure 22:
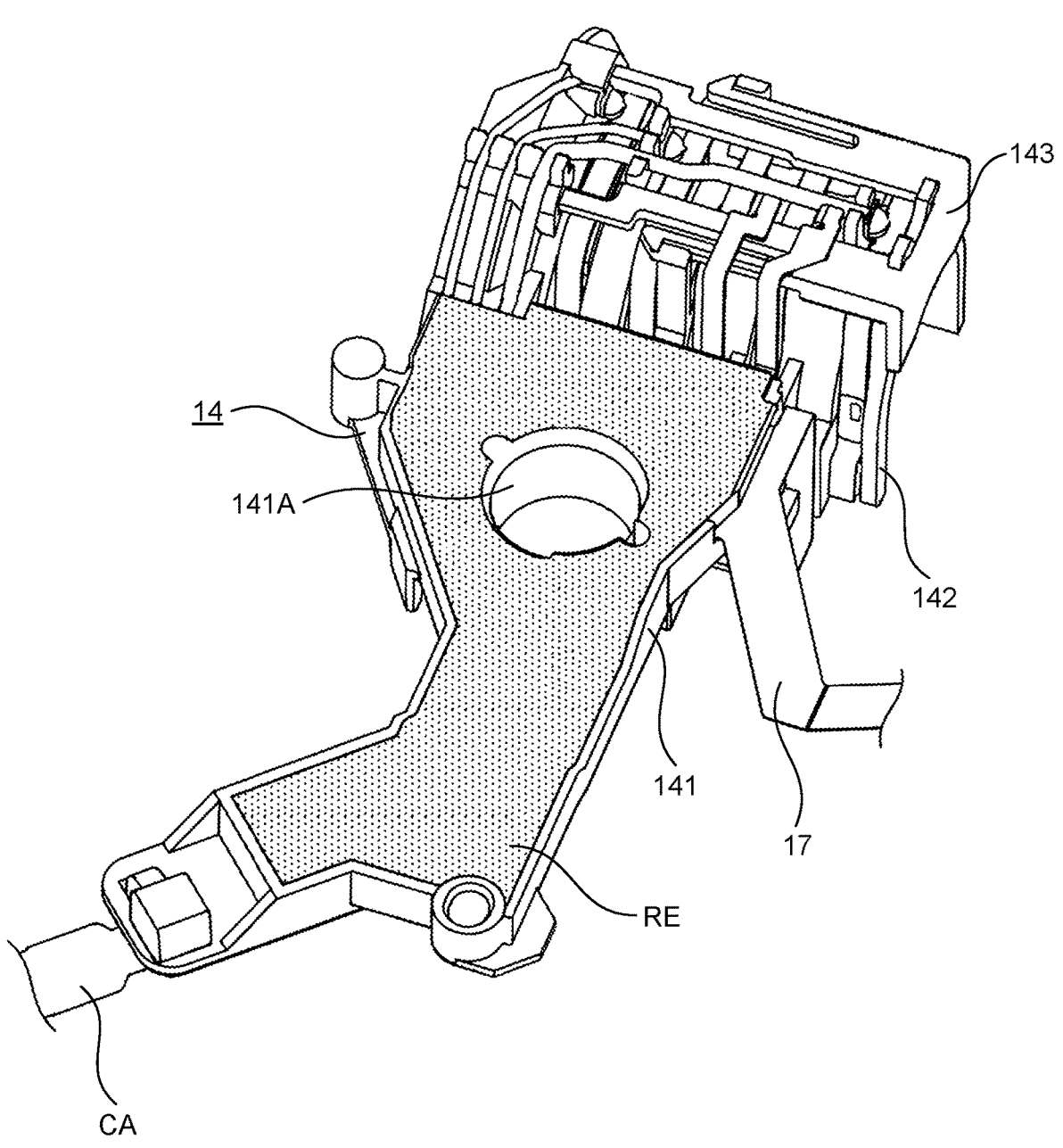
FIG. 22 is a diagram illustrating the method of manufacturing the energy treatment tool.

After Step S1C, the operator coats a plate surface of the base member main body 141 with the resin RE, such as epoxy resin, as illustrated in FIG. 22, the plate surface being on a side where the circuit board 16 has been installed (Step S1D).

Step S2

At Step S2, an operator assembles the energy treatment tool 2 at the second place, as described below.

The operator installs the base unit 13 that has been assembled at Step S1, from the positive direction along the Y-axis, into the first housing 63 (Step S2A).

After Step S2A, the operator installs a unit having the rotating knob 9, the sheath 10, the jaw 11, and the ultrasound probe 12 that have been integrated with one another, from the positive direction along the Y-axis, into the first housing 63 (Step S2B). When this is done, an end portion of the ultrasound probe 12, the end portion being in the proximal direction Ar2, is arranged inside the second terminal holding portion 142, through the notched portion 142J formed in the second terminal holding portion 142.

After Step S2B, the operator attaches the second housing 64 to the first housing 63 (Step S2C). Furthermore, the pair of third switches 8C are respectively installed in the first and second housings 63 and 64.

As described above, at Steps S2A to S2C, the unit having the base unit 13, the rotating knob 9, the sheath 10, the jaw 11, and the ultrasound probe 12 integrated with one another and the second housing 64 are all installed from the same direction (the positive direction along the Y-axis) relatively to the first housing 63.

The energy treatment tool 2 is manufactured by the above Steps S1 and S2.

The above described first embodiment has the following effects.

The pair of third switches 8C in the energy treatment tool 2 according to the first embodiment are set in the first state (the state illustrated with the solid line in FIG. 14 or FIG. 15) or the second state (the state illustrated with the dash-dotted line in FIG. 14 or FIG. 15) in response to a changing operation by an operator, such as a surgeon. Furthermore, the pair of third switches 8C are moved in association with each other in response to the changing operation, by the switch supporting portion 18 described above. Therefore, an operator, such as a surgeon, is able to determine which output state the output state of energy currently is (whether the output state is in the high output mode or the low output mode) by checking whether any of the pair of third switches 8C is in the first state or the second state.

Accordingly, the energy treatment tool 2 according to the first embodiment has an effect of enabling user friendliness to be improved by allowing an operator, such as a surgeon, to readily determine the current energy output state.

Furthermore, the third switch element SW3 in the energy treatment tool 2 according to the first embodiment is formed of the part of the first electric wiring SL1' and the part of the third electric wiring SL3' (FIG. 10), and the metallic contact 19 attached to the switch supporting portion 18, the parts being exposed to the outside of the flexible board 17.

Therefore, the third switch element SW3 is able to be formed of an uncomplicated structure.

Furthermore, the pair of third switches 8C in the energy treatment tool 2 according to the first embodiment are rotatably supported about the third rotation axis Rx3 at the central position in the interior of the holding case 6 along the Y-axis, by the bearing hole 141A and the columnar shaft 181A.

Therefore, in the case where the pair of third switches 8C configured to move in association with each other are adopted, even when a changing operation is performed on any of the pair of third switches 8C, the changing operation is able to be performed smoothly with reduced wobbliness in the pair of third switches 8C.

Furthermore, the pair of third switches 8C in the energy treatment tool 2 according to the first embodiment are provided in a state where they face each other along the Y-axis, and are exposed to the outside of the holding case 6 respectively from the first and second housings 63 and 64.

Therefore, whichever one of the right hand or the left hand of an operator, such as a surgeon, is used to hold the fixed handle 62, a changing operation is able to be performed. Accordingly, the user friendliness is able to be improved even further.

Furthermore, the switch supporting portion 18 in the energy treatment tool 2 according to the first embodiment includes the spring portion 182 having the protruding portion 182A. The base member 14 includes the first engagement recessed portion 144A that maintains the first state by engaging with the protruding portion 182A in the first state (the state illustrated in FIG. 16), and the second engagement recessed portion 144B that maintains the second state by engaging with the protruding portion 182A in the second state (the state illustrated in FIG. 17). According to the engagement of the protruding portion 182A with the first or second engagement recessed portion 144A or 144B, the spring portion 182 provides vibration to the pair of third switches 8C. That is, a click feeling is given to the operator operating the pair of third switches 8C.

Therefore, the operator, such as a surgeon, is able to recognize that the pair of third switches 8C have been set to the first state or the second state. Accordingly, the user friendliness is able to be improved even further.

Second Embodiment

A second embodiment will be described next.

In the following description, any component that is the same as that of the above described first embodiment will be assigned with the same reference sign, and detailed description thereof will be omitted or simplified.

Figure 23:
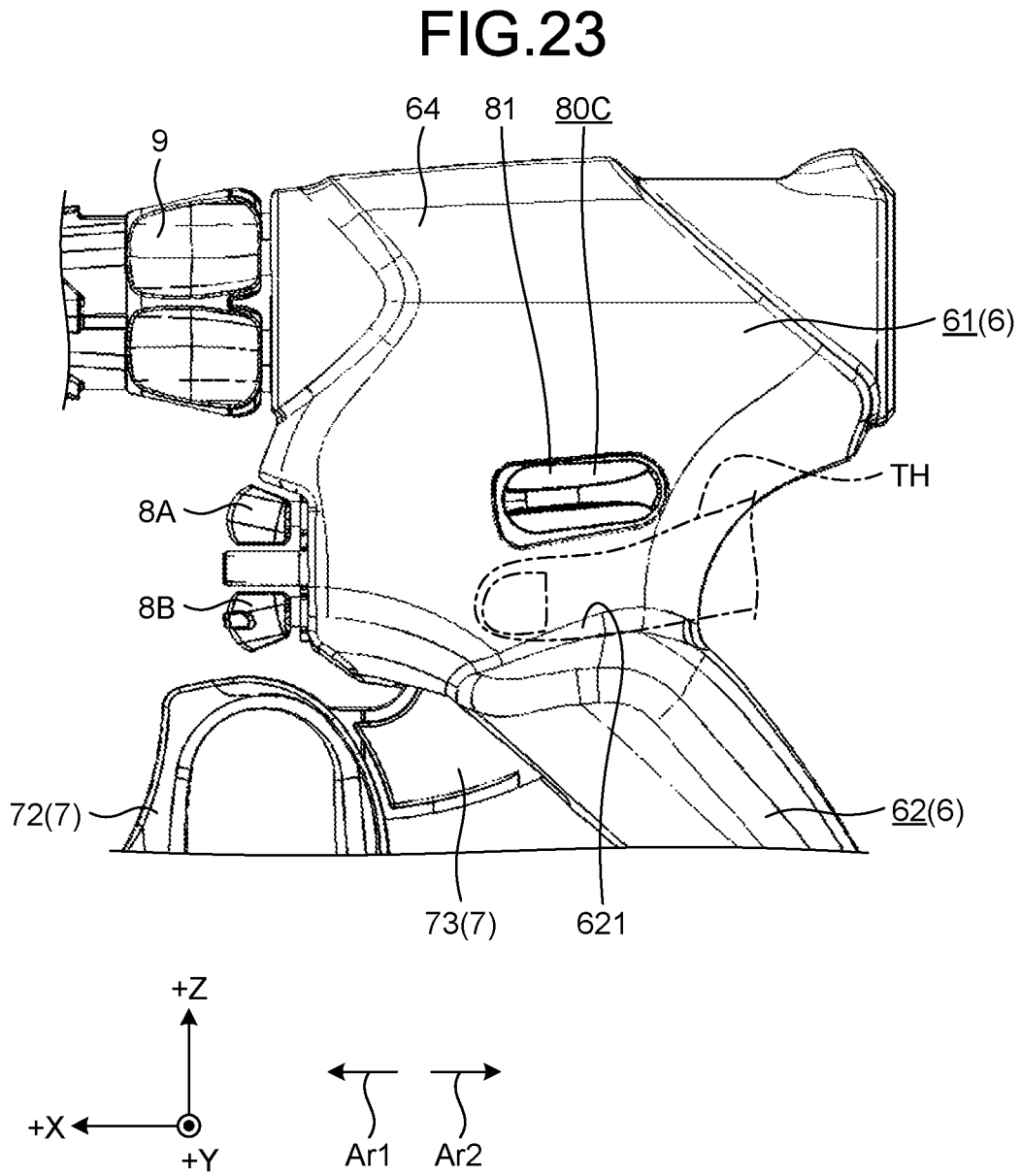
FIG. 23 is a diagram illustrating a support structure of a third switch according to a second embodiment.
Figure 24:
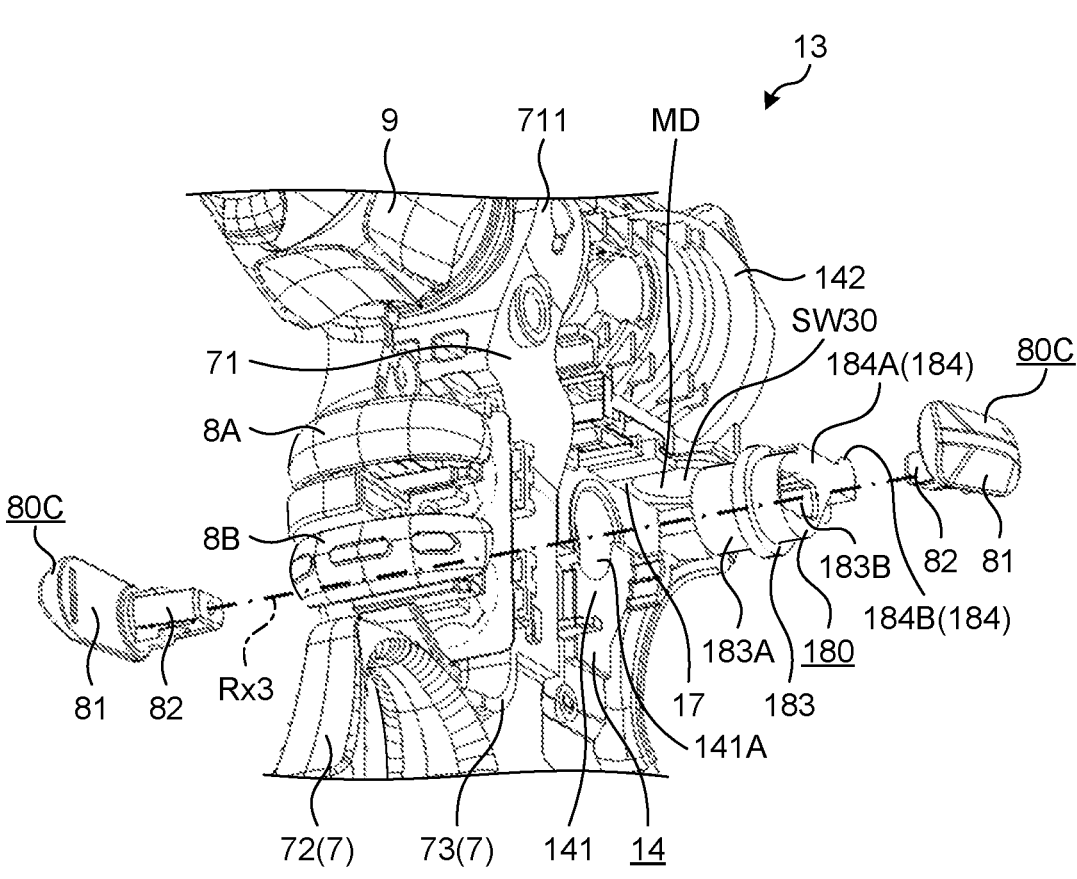
FIG. 24 is a diagram illustrating the support structure of the third switch according to the second embodiment.
Figure 24:
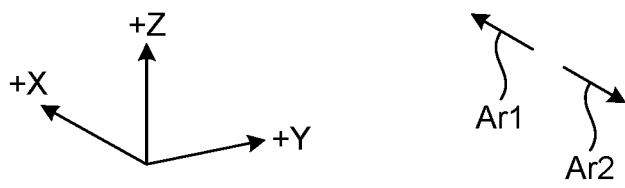
Figure 25:
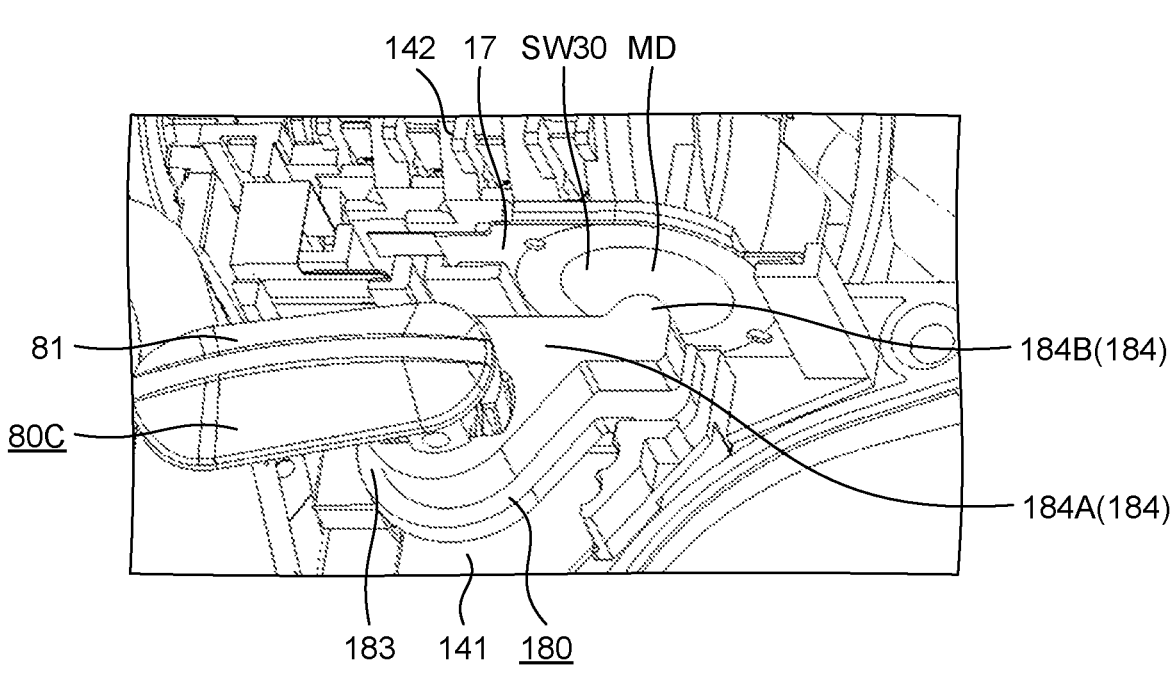
FIG. 25 is a diagram illustrating the support structure of the third switch according to the second embodiment.
Figure 25:
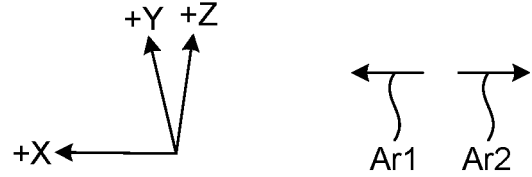

FIG. 23 to FIG. 25 are diagrams illustrating a support structure of the third switches 8C, according to the second embodiment. Specifically, FIG. 23 is a diagram of a holding case 6 as viewed from the positive direction along the Y-axis. FIG. 24 is a diagram illustrating the interior of the holding case 6. FIG. 25 is a diagram of a switch supporting portion 180 as viewed from the positive direction along the Y-axis.

The support structure (the switch supporting portion 18) of the pair of third switches 8C according to the first embodiment described above is made different in this second embodiment. Furthermore, due to the change in the support structure, the configuration of the third switch element SW3 is also changed.

For convenience of explanation, a third switch according to the second embodiment will hereinafter be referred to as a third switch 80C (FIG. 23 and FIG. 24). Furthermore, the switch supporting portion 18 will be referred to as the switch supporting portion 180 (FIG. 24 and FIG. 25) in this second embodiment. In addition, a third switch element according to the second embodiment will be referred to as a third switch element SW30 (FIG. 24 and FIG. 25).

The pair of third switches 80C correspond to a first lever, a second lever, and a lever. The pair of third switches 80C have the same shape. The third switch 80C has a pinched portion 81 having a shape different from that of the third switch 8C described above with respect to the first embodiment.

Specifically, the pinched portion 81 forming the third switch 80C extends in a direction approximately parallel to the central axis Ax and has an approximately rectangular shape when viewed along the Y-axis, as illustrated in FIG. 23 or FIG. 24.

The switch supporting portion 180 corresponds to a driver. The switch supporting portion 180 has a shape different from that of the switch supporting portion 18 described above with respect to the first embodiment.

Specifically, the switch supporting portion 180 includes, as illustrated in FIG. 24, a supporting portion main body 183 and a protruding portion 184.

The supporting portion main body 183 has, as illustrated in FIG. 24, an approximately cylindrical shape extending along the Y-axis. A columnar shaft 183A and a fitting hole 183B similar to the columnar shaft 181A and fitting hole 181B described above with respect to the first embodiment are provided in the supporting portion main body 183. That is, similarly to the switch supporting portion 18 described above with respect to the first embodiment, the columnar shaft 183A is pivotally supported by the bearing hole 141A (FIG. 24) and the switch supporting portion 180 is rotatable about the third rotation axis Rx3 (FIG. 24). Furthermore, the pair of third switches 80C are supported to rotate about the third rotation axis Rx3 at the central position in the holding case 6 along the Y-axis by the bearing hole 141A and the columnar shaft 183A.

The protruding portion 184 includes, as illustrated in FIG. 24 or FIG. 25, an extending portion 184A extending in the proximal direction Ar2 from an end portion of the supporting portion main body 183, the end portion being in the proximal direction Ar2, and a plunger portion 184B protruding in the positive direction along the Z-axis from a tip of the extending portion 184A and having a tip with an arc shape as viewed from a direction along the Y-axis.

The third switch element SW30 is installed on the flexible board 17 (FIG. 24 or FIG. 25) at a position facing the plunger portion 184B. Furthermore, the third switch element SW30 is a switch element having a metal dome MD (FIG. 24 or FIG. 25) and is brought into a state where the first and third electric wirings SL1' and SL3' are electrically connected to each other (a contact state) or a state where they are electrically disconnected (a noncontact state) to each other according to an operation on the third switch element SW30. The third switch element SW30 is a contact that generates a signal to change the output state of energy and corresponds to a second contact.

That is, when a portion of the third switch 80C is moved by an operator, such as a surgeon, with the operator's thumb, in the negative direction along the Z-axis, the portion being in the distal direction Ar1 (when a changing operation is performed by an operator, such as a surgeon), the switch supporting portion 180 is rotated such that the plunger portion 184B is moved in the positive direction along the Z-axis. When this happens, the plunger portion 184B presses the third switch element SW30 while elastically deforming the metal dome MD. That is, the first and third electric wirings SL1' and SL3 are electrically connected to each other.

When the operator, such as a surgeon, removes the operator's thumb from the third switch 80C, the switch supporting portion 180 is rotated such that the plunger portion 184B is moved in the negative direction along the Z-axis due to reactive force by which the metal dome MD attempts to return to its original shape. The pressed state of the third switch element SW30 by the plunger portion 184B is thus cancelled. That is, the first and third electric wirings SL1' and SL3' are brought into a state where the first and third electric wirings SL1' and SL3' are electrically disconnected to each other.

The control device 3 then switches the output mode to one of the high output mode and the low output mode in the state where the first and third electric wirings SL1' and SL3' have been connected to each other, similarly to the first embodiment described above. Furthermore, the control device 3 performs switching to the other one of the high output mode and the low output mode in the state where the first and third electric wirings SL1' and SL3' have been electrically disconnected to each other.

The change of the output state of energy in response to an operation on the third switch 80C is not necessarily the above described switching to the high output mode or low output mode, and similarly to the first and second switches 8A and 8B, may be switching to start of output or stop of output of energy. Furthermore, the third switch 80C may be used as described below.

When the first switch 8A is pressed, the control device 3 causes ultrasound energy and high frequency energy to be applied to a target site. Furthermore, when the first switch 8A is pressed in a state where the portion of the third switch 80C has been moved in the negative direction along the Z-axis (a state where the third switch element SW30 has been pressed), the portion being in the distal direction Ar1, the control device 3 causes only the ultrasound energy to be applied to the target site. That is, the output states of energy for when the first and third switches 8A and 80C have been pressed concurrently and for when only the first switch 8A has been pressed may be made different from each other.

Furthermore, as illustrated in FIG. 23, a finger rest surface 621 for an operator, such as a surgeon, to rest the operator's thumb TH when the operator holds the fixed handle 62 is provided at a boundary between the holding case main body 61 and the fixed handle 62, on an outer surface of the holding case 6 according to the second embodiment.

This finger rest surface 621 is formed of a curved surface having its normal direction directed in the positive direction along the Z-axis. The third switch 80C and the finger rest surface 621 are arranged such that the thumb TH is placed between the third switch 80C and the finger rest surface 621 in a state where the thumb TH has been rested on the finger rest surface 621.

Effects that are similar to those of the above described first embodiment are also achieved when the above described configuration of the second embodiment is adopted.

Other Embodiments

Modes for carrying out the embodiments have been described above, but the disclosure is not to be limited only to the above described first and second embodiments.

Figure 26:
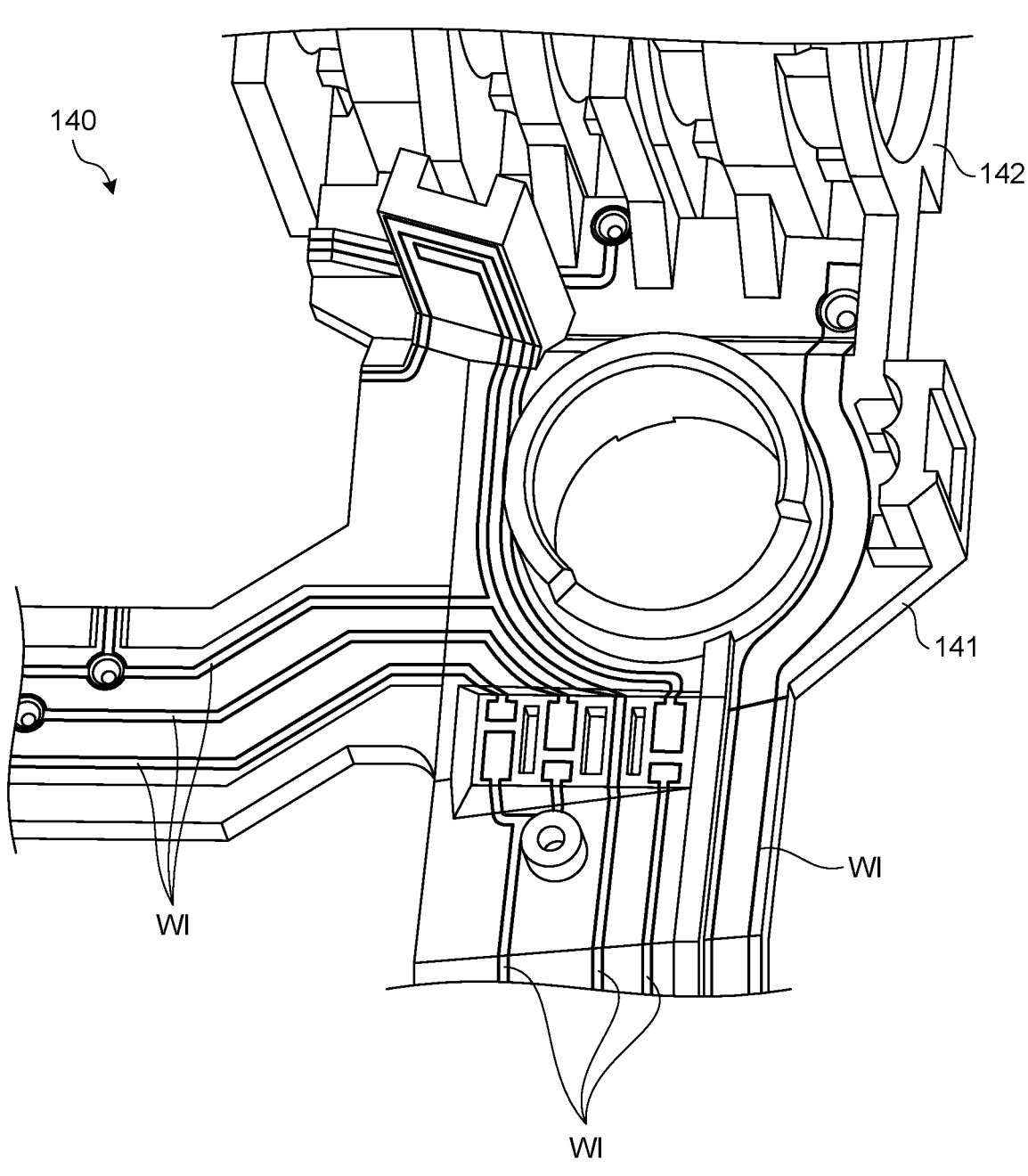
FIG. 26 is a diagram illustrating a modified example of the first or second embodiment.

FIG. 26 is a diagram illustrating a modified example of the first or second embodiment.

In the first or second embodiment described above, a base member 140 illustrated in FIG. 26 may be adopted instead of the base member 14.

The base member 140 according to this modified example is formed of a molded interconnect device (MID). That is, the base member 140 is formed of a resin molding having wirings WI formed on its outer surface, as illustrated in FIG. 26.

In the above described first or second embodiment, the configuration for applying both ultrasound energy and high frequency energy to a target site is adopted as an energy treatment tool according to the disclosure, but without being limited to this configuration, a configuration for applying at least one of ultrasound energy, high frequency energy, and thermal energy may be adopted. "Applying thermal energy to a target site" herein means transmitting heat generated in a heater, for example, to a target site.

In the above described first or second embodiment, the configuration including, in addition to the base member main body 141, the second terminal holding portion 142 and the terminal holding member 143 is adopted as a base member according to the disclosure, but without being limited to this configuration, the base member may be formed of just the base member main body 141 without the second terminal holding portion 142 and terminal holding member 143.

Figure 27:
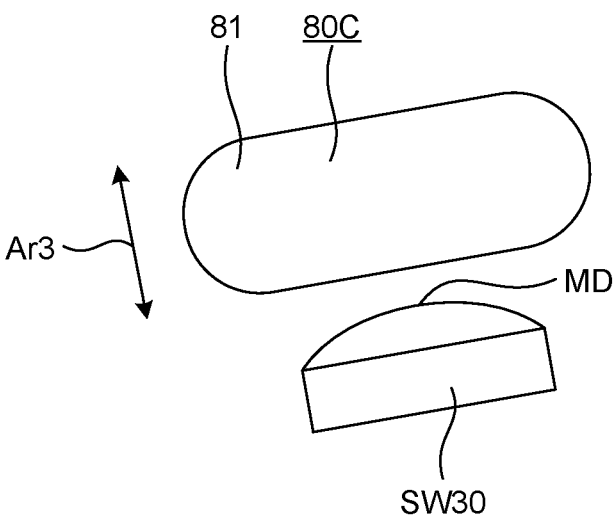
FIG. 27 is a diagram illustrating a modified example of the first or second embodiment.
Figure 28:
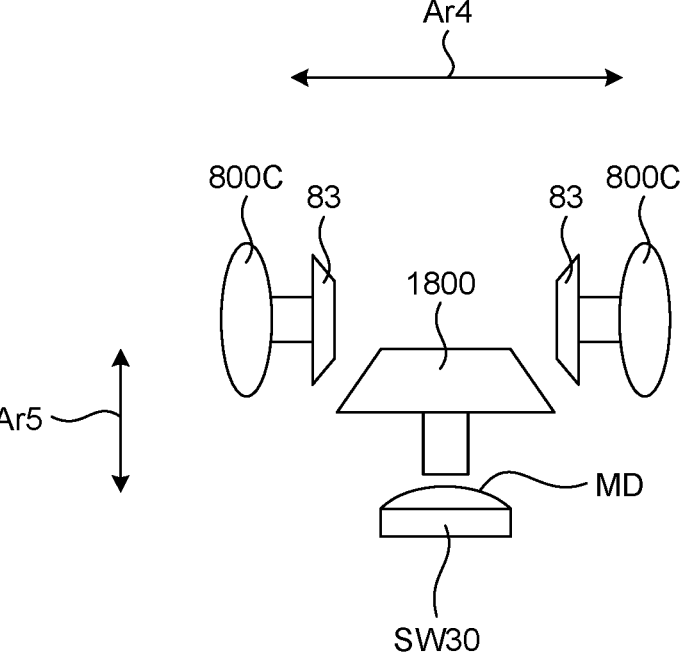
FIG. 28 is a diagram illustrating a modified example of the first or second embodiment.

FIG. 27 and FIG. 28 are diagrams illustrating modified examples of the first or second embodiment.

The pair of third switches 80C and the switch supporting portion 180 in the second embodiment described above are configured to be rotatable about the third rotation axis Rx in response to a changing operation by an operator, such as a surgeon, but the second embodiment is not limited to this configuration.

For example, the pair of third switches 80C and the switch supporting portion 180 may be configured to press the third switch element SW30 by sliding in a direction of an arrow Ar3, as illustrated in FIG. 27, in response to a changing operation by an operator, such as a surgeon.

Furthermore, for example, a pair of third switches 800C may be configured to be slidable in a direction of an arrow Ar4 in response to a changing operation by an operator, such as a surgeon, as illustrated in FIG. 28. In addition, instead of the switch supporting portion 180, a driver 1800 may be provided, the driver 1800 being slidable in a direction of an arrow Ar5 by being pressed by plunger portions 83 provided in the third switches 800C correspondingly to the movement of the pair of third switches 800C in the direction of the arrow Ar4. By the sliding of the driver 1800, the third switch element SW30 is pressed.

These structures in FIG. 27 and FIG. 28 may also be applied to the first embodiment described above.

An energy treatment tool and a treatment system according to the disclosure have an effect of being able to improve user friendliness.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy treatment tool, comprising:
a grip and a movable trigger portion connected to the grip on a distal side of the grip, the grip being configured to be held by an operator;
a sheath attached to the grip and extending along a second axis;
a lever that is provided on a lateral side surface of the grip, the lever being configured to rotate about a first axis that intersects the second axis in a three-dimensional manner, in response to a changing operation by an operator, the changing operation being performed for changing an output state of energy;
a switch element that is arranged inside the grip, the switch element being configured to generate a signal for changing an output state of the energy; and
a switch supporting portion that is arranged entirely inside the grip such that the switch supporting portion is configured to rotate about the first axis that intersects the second axis, the switch supporting portion being configured to move in response to a movement of the lever, the switch supporting portion being configured to switch the switch element between an electrically connected state and an electrically disconnected state.

2. The energy treatment tool according to claim 1, further comprising a base arranged inside the grip, the switch supporting portion being attached to the base.

3. The energy treatment tool according to claim 1, wherein the switch element includes a metal dome to be pressed by the switch supporting portion.

4. The energy treatment tool according to claim 1, further comprising an output switch that is provided outside of the grip, the output switch being configured to switch between starting output of the energy and stopping the output of the energy by moving in a direction along the longitudinal axis.

5. The energy treatment tool according to claim 1, wherein:
the grip includes a finger rest surface, the finger rest surface being configured to allow the operator is to rest a thumb of the operator, and
the lever and the finger rest surface are arranged such that the thumb is placed between the lever and the finger rest surface in a state where the thumb has been rested on the finger rest surface.

6. The energy treatment tool according to claim 1, wherein
the grip comprises a first housing that faces a second housing and form side surfaces of the grip, and
the lever further comprises:
a first lever exposed from the first housing; and
a second lever exposed from the second housing.

7. The energy treatment tool according to claim 6, wherein:
a base arranged inside the grip includes a bearing hole formed in the base, the bearing hole penetrating through the base, and
the switch supporting portion includes a columnar shaft that is inserted through the bearing hole and rotatably supported about an axis by the bearing hole, and
the switch supporting portion is configured to rotate in response to movement of the first lever and the second lever.

8. The energy treatment tool according to claim 7, wherein the bearing hole is positioned inside the grip at a center portion between the first housing and the second housing.

9. The energy treatment tool according to claim 6, wherein the first lever and the second lever are attached to the switch supporting portion such that the first lever and the second lever rotate integrally with the switch supporting portion in response to the changing operation.

10. The energy treatment tool according to claim 6, wherein:
the first lever, the second lever, and the switch supporting portion are each configured to be set in a first state or a second state by moving in response to the changing operation, and
the energy treatment tool further comprises:
a protruding portion provided in the switch supporting portion;
a first engagement recessed portion that is provided in a base member arranged in the grip, the first engagement recessed portion being configured to maintain the first state by engaging with the protruding portion in the first state; and
a second engagement recessed portion that is provided in the base member, the second engagement recessed portion being configured to maintain the second state by engaging with the protruding portion in the second state.

11. The energy treatment tool according to claim 10, further comprising:

a spring portion that includes the protruding portion or the first and second engagement recessed portions, wherein:

the spring portion is elastically deformable, and the spring portion is configured to provide vibration to the first lever, the second lever, and the switch supporting portion when the protruding portion engages with the first engagement recessed portion and when the protruding portion engages with the second engagement recessed portion.

12. The energy treatment tool according to claim 6, wherein:

the first lever, the second lever, and the switch supporting portion are each configured to be set in a first state or a second state by moving in response to the changing operation, and the energy treatment tool further comprises:

a protruding portion provided in a base member arranged inside the grip;

a first engagement recessed portion that is provided in the switch supporting portion, the first engagement recessed portion being configured to maintain the first state by engaging with the protruding portion in the first state; and a second engagement recessed portion that is provided in the switch supporting portion, the second engagement recessed portion being configured to maintain the second state by engaging with the protruding portion in the second state.

13. The energy treatment tool according to claim 12, further comprising:

a spring portion that includes the protruding portion or the first and second engagement recessed portions, wherein:

the spring portion is elastically deformable, and the spring portion is configured to provide vibration to the first lever, the second lever, and the switch supporting portion when the protruding portion engages with the first engagement recessed portion and when the protruding portion engages with the second engagement recessed portion.

14. A treatment system, comprising:

the energy treatment tool according to claim 1; and a controller configured to control operation of the energy treatment tool.

15. The energy treatment tool according to claim 1, further comprising:

an end effector attached to a distal part of the energy treatment tool;

a rotary knob disposed on a distal part of the grip, the rotary knob being configured to rotate the end effector, wherein the lever is configured to rotate about the first axis.

16. The energy treatment tool according to claim 1, comprising:

wherein the lateral side surface being perpendicular to the distal side to which the trigger portion is connected, the switch element is arranged entirely inside the grip, and the switch supporting portion is connected to the lever.

17. The energy treatment tool according to claim 1, wherein the lever is rotatable between the first position for an ON state engaging the electrically connected state and the second position for an OFF state engaging the electrically disconnected state.

18. The energy treatment tool according to claim 1, wherein both the lever and a trigger-side switch are switches configured to turn the output state of the energy on or off.

19. The energy treatment tool according to claim 1, wherein the first axis is fixed to the grip.

* * * * *